(12) United States Patent
Acosta et al.

(10) Patent No.: US 7,842,626 B2
(45) Date of Patent: *Nov. 30, 2010

(54) PARTIALLY FLUORINATED COMPOSITIONS AND SURFACE ACTIVE AGENTS

(75) Inventors: Erick Jose Acosta, New Castle, DE (US); Anilkumar Raghavanpillai, Greenville, DE (US); Sheng Peng, Wilmington, DE (US); Stefan Reinartz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1052 days.

This patent is subject to a terminal disclaimer.

(21) Appl. No.: 11/598,407

(22) Filed: Nov. 13, 2006

(65) Prior Publication Data
US 2008/0113172 A1 May 15, 2008

(51) Int. Cl.
*B32B 5/02* (2006.01)
*C08L 27/12* (2006.01)
(52) U.S. Cl. ............... 442/91; 442/85; 442/86; 442/94; 442/82; 524/544
(58) Field of Classification Search ............ 442/93, 442/94, 91, 85, 86, 82
See application file for complete search history.

(56) References Cited

U.S. PATENT DOCUMENTS

| | | | |
|---|---|---|---|
| 3,253,978 A | 5/1966 | Bodendorf et al. | |
| 3,338,825 A | 8/1967 | Taggart | |
| 3,979,469 A | 9/1976 | Jager | |
| 4,587,366 A | 5/1986 | von Werner | |
| 5,459,212 A | 10/1995 | Krespan et al. | |
| 5,481,028 A | 1/1996 | Petrov et al. | |
| 5,885,909 A | 3/1999 | Rudisill et al. | |
| 6,025,521 A | 2/2000 | Krespan et al. | |
| 6,420,466 B1 | 7/2002 | Haubennestel et al. | |
| 6,548,431 B1 | 4/2003 | Bansal et al. | |
| 6,797,655 B2 | 9/2004 | Rudisill et al. | |
| 6,831,025 B2 | 12/2004 | Rudisill et al. | |
| 7,473,658 B2 * | 1/2009 | Acosta et al. ............ | 442/93 |
| 2004/0038014 A1 | 2/2004 | Schaefer et al. | |
| 2006/0096260 A1 | 5/2006 | Bryner et al. | |

FOREIGN PATENT DOCUMENTS

| | | |
|---|---|---|
| GB | 1097679 | 1/1968 |
| WO | WO 95/11877 | 5/1995 |
| WO | WO 03/080905 A1 | 10/2003 |
| WO | 2006/116222 | 2/2006 |

OTHER PUBLICATIONS

Honda et al., "Molecular Aggregation Structure and Surface Properties of Poly(fluoroalkyl acrylate) Thin Films", Macromolecules, vol. 38 (2005), pp. 5699-5705.
Carey et al., "Amino-Protecting Groups", Chapter 13, Multistep Syntheses, Advanced Organic Chemistry, $3^{rd}$ Edition, Part B, Plenum Press, NY, (1990), pp. 686-689.
Afonso et al., "Kinetics and mechanism of thermal gas-phase oxidation of hexafluoropropene in the presence of trifluoromethylhypofluorite, CF3OF", Phys. Chem. Chem. Phys., vol. 2, (2000), pp. 1393-1399.
Balague et al., "Synthesis of fluorinated telomers. Part 1. Telomerization of vinylidene fluoride with perfluoroalkyl iodides", J. Fluorine Chem., vol. 70, (1995), pp. 215-223.
Trabelsi et al., J. Fluorine Chem., vol. 69, (1994), pp. 115-117 (Abstract in English).
Goshe et al., "Supramolecular recognition: On the kinetic lability of thermodynamically stable host-guest association complexes", Proc. Nat. Acad. Sci. USA, vol. 99, No. 8, (2002), pp. 4823-4929.
Adamson, Physical Chemistry of Surfaces, $4^{th}$ edition, John Wiley & Sons, (1982), pp. 330-361.
Jouani et al., J. Fluorine Chem., vol. 56, (1992) pp. 85-92 (Abstract in English).
Balague et al., Synthesis of Fluorinated Telomers. Part 1. Telomerization of Vinylidene Fluoride With Perfluoroalkyl Iodides, Journal of Fluorine Chemistry, 1995, pp. 215-223, vol. 70.
Balague et al., Controlled Step-Wise Telomerization of Vinylidene Fluoride, Hexafluoropropene and Trifluoroethylene With Iodofluorinated Transfer Agents, Journal of Fluorine Chemistry, 2000, 253-268, vol. 102.
Ameduri et al., First MALDI-TOF Mass Spectrometry of Vinylidene Fluoride Telomers Endowed With Low Defect Chaining, Macromolecules, 2004, pp. 7602-7609, vol. 37.
Huang et al., Synthesis and Repellent Properties of Vinylidene Fluoride-Containing Polyacrylates, Journal of Fluorine Chemistry, 2007, pp. 1469-1477, vol. 128.

* cited by examiner

*Primary Examiner*—Lynda Salvatore
(74) *Attorney, Agent, or Firm*—Gail D. Tanzer

(57) ABSTRACT

Partially fluorinated amino acid derivatives are provided that are useful as organogelators and surface treatment materials to provide oil- and water- repellency properties to substrates. Also provided are composite materials comprising a porous support and a porous nanoweb. The porous nanoweb contains fibrous structures of about 10 nm to about 1000 nm effective average fiber diameter.

14 Claims, 2 Drawing Sheets

$R^4$ = t-butyl

PARTIALLY FLUORINATED COMPOSITIONS AND SURFACE ACTIVE AGENTS

FIELD OF INVENTION

The present invention relates to fluorinated compounds containing short perfluorinated alkyl chains that are useful as organogelators and surface treatment materials to provide oil- and water-repellency properties to substrates.

BACKGROUND

Various compositions are known to be useful as treating agents to provide surface effects to substrates. Surface effects include repellency to moisture, soil, and stains, and other effects, which are particularly useful for fibrous substrates and other substrates such as hard surfaces. Many such treating agents are fluorinated polymers or copolymers.

Most commercially available fluorinated polymers useful as treating agents for imparting repellency to substrates contain predominately eight or more carbons in the perfluoroalkyl chain to provide the desired repellency properties. Honda et al, in Macromolecules, 2005, 38, 5699-5705 disclose that for perfluoroalkyl chains of greater than 8 carbons, orientation of the $R_f$ groups is maintained in a semi-crystalline configuration while for such chains having less than 6 carbon atoms, reorientation occurs.

Various attempts have been made to improve particular surface effects and to increase the fluorine efficiency; i.e., boost the efficiency or performance of treating agents so that lesser amounts of the expensive fluorinated polymer are required to achieve the same level of performance or have better performance using the same level of fluorine. It is desirable to reduce the chain length of the perfluoroalkyl groups thereby reducing the amount of fluorine present, while still achieving the same or superior surface effects. Use of shorter chain perfluoroalkyl groups is one way to reduce the amount of fluorine present. Other approaches provide alternative mechanisms for structure and ordering in the fluorinated materials having short fluorinated tails. For instance, one approach is to combine the characteristics of structures known to undergo gelation via, for instance, hydrogen bonding, with short perfluorinated alkyl moieties. The ordering imposed upon the perfluorinated alkyl groups by the hydrogen bonding networks may amplify the ability of the perfluorinated alkyl moieties to order, thus increasing the fluorine efficiency of surface treating agents comprising such structures.

There is a continuing need for compositions that improve the repellency and stain resistance of treating agents for fibrous and/or porous substrates and hard surface substrates while using lower levels of fluorine. The present invention is directed to these, and other, important ends.

SUMMARY OF INVENTION

One aspect of the invention is a composition of formula (I)

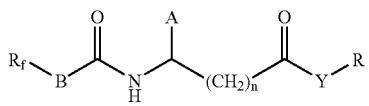

(I)

wherein A is selected from the group consisting of: hydrogen, $C_1$-$C_5$ straight and branched chain alkyl, phenyl, benzyl, and —C(O)—Y—R;
Y is independently —O— or —NH—;
n is an integer of 0 to 10;
R is a monovalent group having 1 to 40 carbon atoms;
B is selected from the group consisting of: —O—, —NH—, and a covalent bond;
$R_f$ is a monovalent group is selected from the group consisting of formulas (IIa), (IIb), (IIc) and (IId):

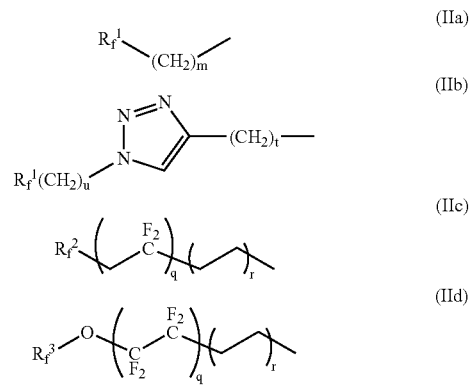

wherein
m is an integer of 0 to 4;
u and t are, independently, integers of 1 to 10;
q and r are, independently, integers of 1 to 3;
$R_f^1$ is a $C_1$-$C_6$ linear or branched perfluoroalkyl group, optionally interrupted by one to five ether oxygen atoms, or a $C_6$ perfluorinated aryl group;
$R_f^2$ is a $C_1$-$C_6$ linear or branched perfluoroalkyl group; and
$R_f^3$ is a $C_1$ to $C_7$ linear or branched perfluoroalkyl group, optionally interrupted by one to three ether oxygen atoms.

Another aspect of the invention is composite material comprising a porous support and a porous nanoweb, wherein said porous nanoweb comprises fibrous structures of about 10 nm to about 1000 nm effective average fiber diameter as determined with electron microscopy; said fibrous structures comprising one or more compositions of formula (I) as described above.

Another aspect of the invention is a solid substrate to which has been applied a composition of formula (I) as described above.

DETAILED DESCRIPTION

Unless otherwise defined, all technical and scientific terms used herein have the same meaning as commonly understood by one of ordinary skill in the art to which this invention pertains. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

In various embodiments, in formula (I), R is selected from the group consisting of: $C_1$-$C_{18}$ linear or branched alkyl groups; $C_1$-$C_{18}$ linear or branched alkyl groups having, or interrupted by, a $C_4$-$C_{16}$ cycloaliphatic group; $C_1$-$C_{18}$ linear or branched alkyl groups having, or interrupted by, a $C_4$-$C_{16}$ aromatic group; $C_1$-$C_{18}$ linear or branched alkyl groups having, or interrupted by, a $C_4$-$C_{16}$ cycloaliphatic group and a $C_4$-$C_{16}$ aromatic group; $C_4$-$C_{16}$ cycloaliphatic group; a $C_4$-$C_{16}$ aromatic group; and $C_4$-$C_{16}$ cycloaliphatic group having a $C_4$-$C_{16}$ aromatic group; wherein each aromatic group is optionally substituted with one or more Cl or Br; each alkyl and cycloaliphatic group is optionally substituted with one or two carbon-carbon double bonds; each group is optionally interrupted by one to four heteroatoms selected from the group: —O— and —$NR^3$—; and each group is optionally interrupted by one to four linkers selected from the group —S—, —N═, —OC(O)—, —C(O)$NR^3$—, —OC(O)$NR^3$—, —$NR^3$C(O)$NR^3$—; wherein $R^3$ is selected from the group consisting of: hydrogen and $C_1$-$C_4$ alkyl group. In various preferred embodiments of the invention A is hydrogen or —C(O)—Y—R; Y is —NH— and R is a $C_6$ to $C_{18}$ linear or branched alkyl group.

Figure 1:
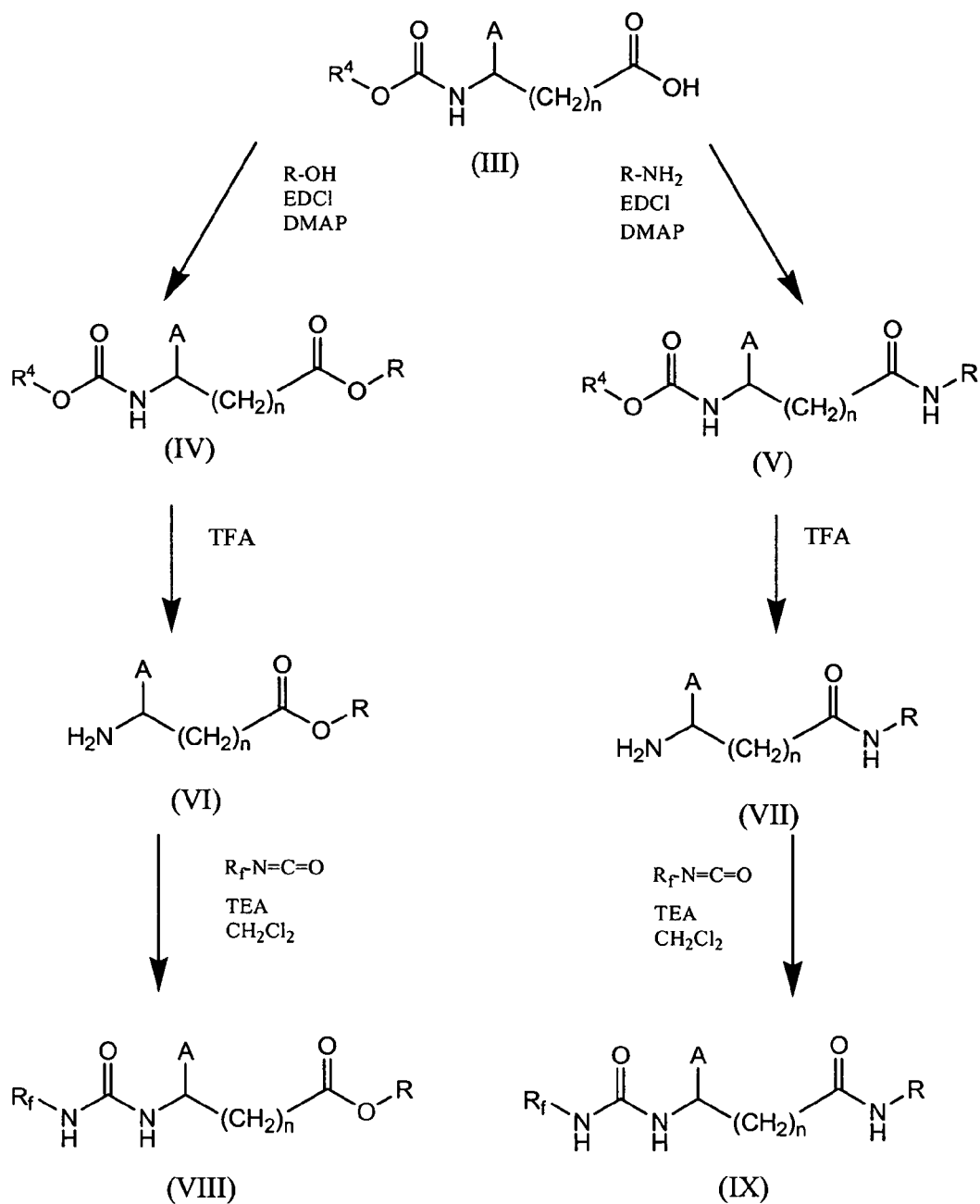
FIG. 1 illustrates the synthesis of some compounds of various embodiments of the invention.

Compositions of various embodiments of the invention can be made using the synthetic scheme illustrated in FIG. 1. Convenient starting materials for the synthesis are t-butyloxycarbonyl (N-BOC)-blocked amino acids of formula (III). They can be provided by treatment of the corresponding amino acids, wherein A and n are described above, with t-butyloxycarbonyl chloride according to the general procedures in "Advanced Organic Chemistry" by Francis A. Carey and Richard J. Sundberg (Third Edition, Part B, page 686, 1990, Plenum Press, New York). Many N-BOC amino acids of formula (III) are available from Aldrich Chemical Co., Milwaukee, Wis. and Genscript Corp., Piscataway N.J., 08854. N-BOC amino acids useful in various embodiments of the invention include those listed in Table 1. Wherein isomers are possible, the N-BOC amino acids may be the D-, L-, the racemic mixture, or any combination thereof. Specifically, N-BOC-aspartic acid includes mixtures of isomers derived from racemic 2-aminosuccinic acid.

TABLE 1

N-BOC amino acids of formula (III).

| Structure | Name |
|---|---|
|  | N-BOC-glycine |
|  | N-BOC-β-alanine |
|  | N-BOC-aspartic acid |
| 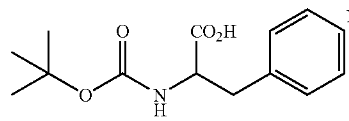 | N-BOC-phenylalanine |
| 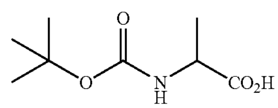 | N-BOC-alanine |
| 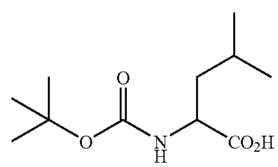 | N-BOC-leucine |
| 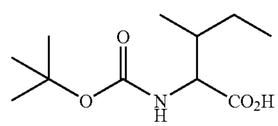 | N-BOC-isoleucine |
| 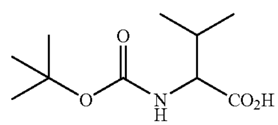 | N-BOC-valine |
| 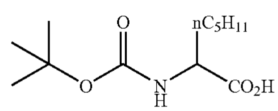 | N-BOC-norleucine |
| 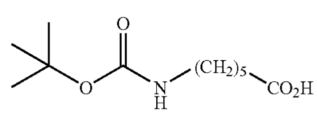 | N-BOC-6-aminohexanoic acid |
| 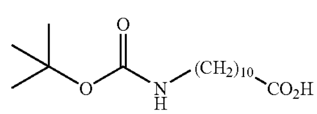 | N-BOC-11-aminoundecanoic acid |

Further considering FIG. 1, condensation of alcohols, designated R—OH, and primary amines, designated R—$NH_2$, respectively, with N-blocked amino acids of formula (III) provide N-BOC-blocked amino esters of formula (IV) and N-BOC-blocked amino amides (V). The condensations are typically run with equivalent amounts of 1-[3-(dimethylamino)propyl]-3-ethylcarbodiimide hydrochloride (EDCl) coupling agent and dimethylaminopyridine (DMAP) as a catalyst, but other carbodiimide coupling agents and heterocyclic or tertiary amines also can be used.

The N-BOC-blocked amino esters (IV) and N-BOC-blocked amino amides (V) can be cleaved with acid, for instance trifluoroacetic acid (TFA), to provide amino esters (VI) and amino amides (VII), respectively, which are useful in synthesis of many compositions of the invention.

Various embodiments of the invention include compositions of formula (VIII) and (IX), illustrated in FIG. 1, that are useful as organogelators and/or surface active agents. These structures are defined by formula (I) with B═—NH—, and A, R, $R_f$, Y, and n defined above. Compositions of formula (VIII) and (IX) can be provided by condensation of fluorinated isocyanates, represented by $R_f$—N═C═O with amino esters (VI) and amino amides (VII), respectively. Typically a tertiary amine, for instance triethylamine (TEA), is used as catalyst, but other catalysts, or no catalyst, can be used if so desired. Typically a nonhydroxylic hydrocarbon solvent such as toluene or xylenes or a halocarbon such as dichloromethane is used in the condensation.

Monoisocyanates useful in the synthesis of compositions of formula (VIII) and (IX) include 1H,1H,2H,2H-perfluorooctylisocyanate, 1H,1H,2H,2H-perfluorohexyl isocyanate, and pentafluorophenyl isocyanate. Others include 1H,1H,2H,2H,3H,3H-perfluoroheptyl isocyanate and 1H,1H,2H,2H,3H,3H-perfluorononyl isocyanate available by synthesis as disclosed by Lucas, et al, in J. Fluorine Chem. 92 (1998) 17-22. The related branched chain alkyl isocyanates disclosed in the aforementioned reference may also be useful in the invention. Preferred compositions of formula (VIII) and (IX) are wherein $R_f$ is formula (IIa), $R_f^1$ is a $C_1$-$C_6$ linear or branched perfluoroalkyl group and m=0 or 2.

Other embodiments of the invention include compositions of formula (XXI) and (XXII), illustrated in scheme 1:

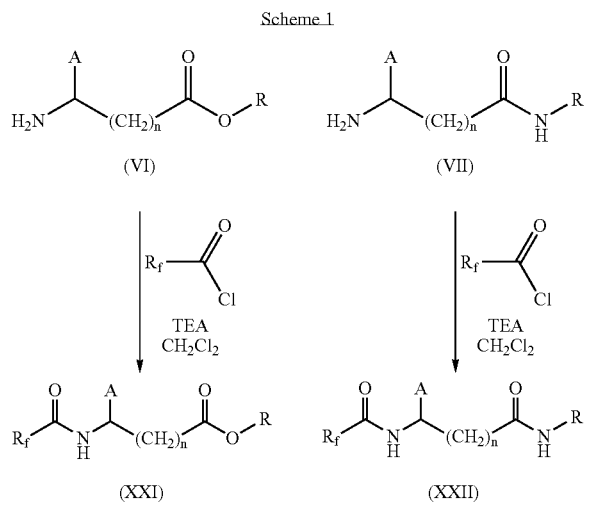

These structures are defined by formula (I) with B=covalent bond, and A, R, $R_f$, Y, and n defined above. Compositions of formula (XXI) and (XXII), can be provided by condensation of fluorinated carboxylic acid chlorides, represented by $R_f$—C(O)—Cl, with amino esters (VI) and amino amides (VII), respectively. Alternatively, fluorinated carboxylic acid fluorides or bromides can be used, is so desired. Typically a tertiary amine, for instance TEA, is used as catalyst, but other catalysts can be used if so desired. Typically a nonhydroxylic hydrocarbon solvent such as toluene or xylenes or a halocarbon such as dichloromethane is used in the condensation.

Fluorinated carboxylic acid halides useful in the synthesis of compositions of formula (XXI) and (XXII) include pentafluorobenzoyl chloride, 2H,2H,3H,3H-perfluorohexanoyl chloride, 2H,2H,3H,3H-perfluoroheptanoyl chloride, 2H,2H,3H,3H-perfluorononoyl chloride, perfluoroheptanoic acid chloride, perfluoropentanoic acid chloride, 2H,2H-perfluoropentanoic acid chloride, 2H,2H-perfluorohexanoic acid chloride, and 2H,2H-perfluorooctanoic acid chloride. Other fluorinated carboxylic acid halides useful in the synthesis of compositions of formula (XXI) and (XXII) include the hexafluoropropylene oxide dimer (compound D1) and the telomer acid fluoride, compound D2 wherein s=1 to 4: The telomer acyl fluorides including compound D2, wherein s=1, are available by synthesis as disclosed in British Pat. No. 1,097,679 and Afonso, et al, Phys. Chem. Chem. Phys., 2000, 2 1393-1399.

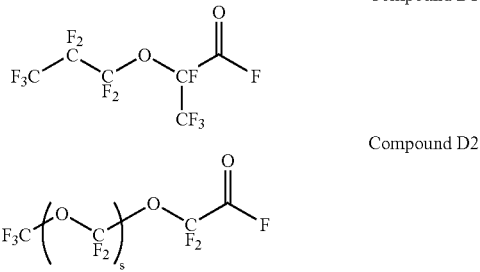

Other useful compounds are the branched telomer acyl fluorides of formula D3, wherein v=1 to 3, that are available by synthesis as described by Resnick, in U.S. Pat. No. 3,692,843.

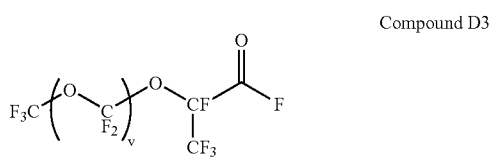

Preferred compositions of formula (I) wherein B=covalent bond are wherein $R_f$ is formula (IIa), m=0 or 2, and $R_f^1$ is a $C_3$-$C_6$ linear or branched perfluoroalkyl group, optionally interrupted by one to five ether oxygen atoms.

Other embodiments include compositions of formula (XXXI) and (XXXII) as illustrated in scheme 2, useful as organogelators and/or surface active agents.

Scheme 2

-continued

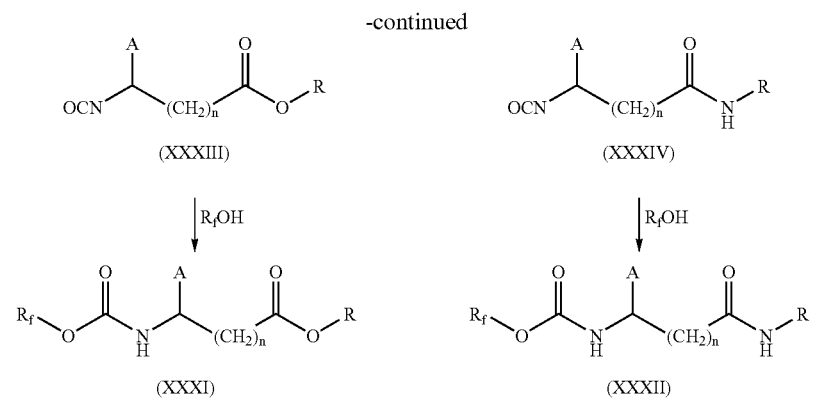

These structures are defined by formula (I) with B=—O—, and A, R, $R_f$, Y, and n defined above. Compositions of formula (XXXI) can be provided by reaction of amino esters (VI) with triphosgene to provide the corresponding isocyanate (XXXIII); followed by condensation of the isocyanate with a fluorinated alcohol, designated $R_f$—OH. Compositions of formula (XXXII) can be provided by reaction of amino amides (VII) with ethyl chloroformate and trimethylsilyl chloride (TMSCl) to provide the corresponding isocyanate (XXXIV) followed by condensation of the isocyanate with a fluorinated alcohol $R_f$—OH.

Fluorinated alcohols, $R_f$—OH, useful in forming compounds of the invention include those of formulas (Xa), (Xb), (Xc) and (Xd):

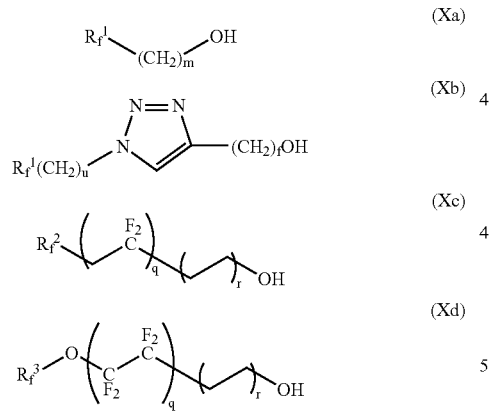

Fluorinated alcohols of formula (Xa) wherein $R_f^1$ is a $C_3$-$C_6$ perfluorinated alkyl or $C_6$ perfluorinated aryl group, and m=0 to 4, include perfluorophenol, 1H,1H,2H,2H-perfluoro-1-pentanol, 1H,1H,2H,2H-perfluoro-1-hexanol, 1H,1H,-perfluoro-1-hexanol 1H,1H,2H,2H-perfluoro-1-octanol. A preferred embodiment of formula (I) is a composition wherein $R_f$ is formula (IIa), B=—O—, m=2 to 4, and $R_f^1$ is a $C_2$-$C_6$ linear or branched perfluoroalkyl group.

Fluorinated triazole alcohols (Xb) can be provided by dipolar cycloaddition reaction of fluoroalkyl alkyl azides with terminal hydroxy alkynes as illustrated in the following scheme.

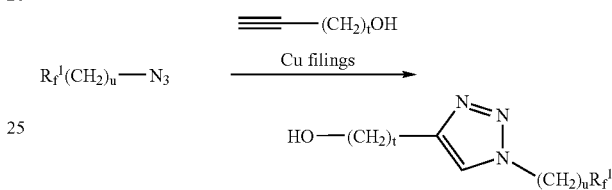

A preferred embodiment of formula (I) is a composition wherein $R_f$ is formula (IIb), B=—O—, and $R_f^1$ is a $C_2$-$C_6$ linear or branched perfluoroalkyl group.

Fluorinated alcohols of formula (Xc), wherein $R_f^2$ is a $C_1$-$C_6$ linear or branched perfluoroalkyl group are available by synthesis according to Scheme 3.

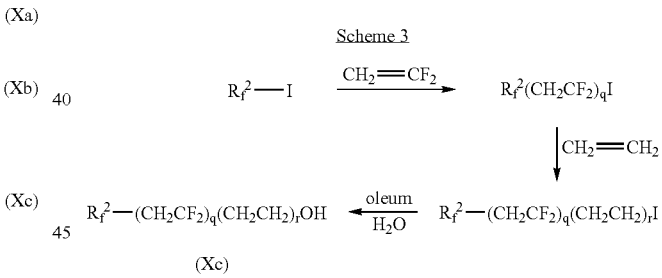

The telomerization of vinylidene fluoride (VDF) with linear or branched perfluoroalkyl iodides is well known, and produces compounds of the structure $R_f^2(CH_2CF_2)_qI$, wherein, q is 1 to 3 or more and $R_f^2$ is a C1 to C6 perfluoroalkyl group. For example, see Balague, et al, "Synthesis of fluorinated telomers, Part 1, Telomerization of vinylidene fluoride with perfluoroalkyl iodides", J. Fluorine Chem. (1995), 70(2), 215-23. The specific telomer iodides are isolated by fractional distillation. The telomer iodides can be treated with ethylene by procedures described in U.S. Pat. No. 3,979,469, (Ciba-Geigy, 1976) to provide the telomer ethylene iodides wherein r is 1 to 3 or more. The telomer ethylene iodides can be treated with oleum and hydrolyzed to provide the corresponding telomer alcohols (Xc) according to procedures disclosed in WO 95/11877 (Elf Atochem S.A.). The higher homologs (q=2, 3) of telomer ethylene iodides are available with excess ethylene at high pressure.

Specific fluorinated telomer alcohols derived from telomerization of vinylidene fluoride and ethylene and useful in the invention are listed in Table 1A. Preferred compositions of formula (I) are wherein $R_f$ is formula (IIc), B=—O—, and $R_f^2$ is a $C_2$-$C_6$ linear or branched perfluoroalkyl group.

TABLE 1A

| Compound No. | Structure |
|---|---|
| A1 | $C_2F_5$–CF$_2$–CH$_2$CH$_2$–OH |
| A2 | $C_2F_5$–(CF$_2$)$_2$–CH$_2$CH$_2$–OH |
| A3 | $C_2F_5$–(CF$_2$)$_3$–CH$_2$CH$_2$–OH |
| A4 | $C_2F_5$–CF$_2$–(CH$_2$CH$_2$)$_2$–OH |
| A5 | $C_2F_5$–(CF$_2$)$_2$–(CH$_2$CH$_2$)$_2$–OH |
| A6 | $C_4F_9$–CF$_2$–CH$_2$CH$_2$–OH |
| A7 | $C_4F_9$–(CF$_2$)$_2$–CH$_2$CH$_2$–OH |
| A8 | $C_4F_9$–(CF$_2$)$_3$–CH$_2$CH$_2$–OH |
| A9 | $C_4F_9$–CF$_2$–(CH$_2$CH$_2$)$_2$–OH |
| A10 | $C_4F_9$–(CF$_2$)$_2$–(CH$_2$CH$_2$)$_2$–OH |
| A11 | $C_6F_{13}$–CF$_2$–CH$_2$CH$_2$–OH |
| A12 | $C_6F_{13}$–(CF$_2$)$_2$–CH$_2$CH$_2$–OH |

TABLE 1A-continued

| Compound No. | Structure |
|---|---|
| A13 | $C_6F_{13}$–(CF$_2$)$_3$–CH$_2$CH$_2$–OH |
| A14 | $C_6F_{13}$–CF$_2$–(CH$_2$CH$_2$)$_2$–OH |
| A15 | $C_6F_{13}$–(CF$_2$)$_2$–(CH$_2$CH$_2$)$_2$–OH |

Fluorinated alcohols of formula (Xd), wherein $R_f^3$ is a $C_1$ to $C_7$ linear or branched perfluoroalkyl group, optionally interrupted by one oxygen atom are available by synthesis according to Scheme 4.

Scheme 4

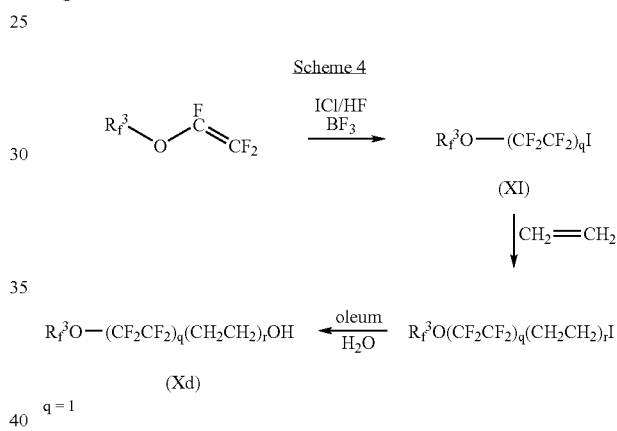

q = 1

The perfluoroalkyl ether ethyl iodides can be made from perfluoroalkyl vinyl ethers by the procedure described in Example 8 of U.S. Pat. No. 5,481,028. In the second reaction in Scheme 4, the iodide (IX) is reacted with an excess of ethylene at an elevated temperature and pressure. While the addition of ethylene can be carried out thermally, the use of a suitable catalyst is preferred. Preferably the catalyst is a peroxide catalyst such as benzoyl peroxide, isobutyroyl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time may vary with the catalyst and reaction conditions, but we have found 24 hours to be adequate. The product may be purified by any method that separates unreacted starting material from the final product, but distillation is preferred. Satisfactory yields up to 80% of theory have been obtained using about 2.7 mols of ethylene per mole of perfluoroalkyl ether iodide, a temperature of 110° C. and autogenous pressure, a reaction time of 24 hours, and purifying the product by distillation. The perfluoroalkylether ethylene iodides can be treated with oleum and hydrolyzed to provide the corresponding alcohols (Xc) according to procedures disclosed in WO 95/11877 (Elf Atochem S.A.). Alternatively, the perfluoroalkylether ethyl iodides can be treated with N-methyl formamide followed by ethyl alcohol/acid hydrolysis. A temperature of about 130° to 160° C. is preferred. Higher homologs of (XI) wherein q=2, 3 or more, are available from telomerization of iodide (XI), wherein q=1, with tetrafluoroethylene. The higher homologs (r=2, 3) of telomer ethylene iodides are available with excess ethylene at high pressure.

Specific fluoroether alcohols useful in forming compounds of the invention include those listed in Table 1B. Preferred compositions of formula (I) are wherein $R_f$ is formula (IId), B=—O—, and $R_f^3$ is a $C_3$-$C_6$ linear or branched perfluoroalkyl group.

TABLE 1B

| Compound No. | Structure |
| --- | --- |
| B1 | $F_3C-O-CF_2-CF_2-CH_2CH_2-OH$ |
| B2 | $F_3C-O-(CF_2-CF_2)_2-CH_2CH_2-OH$ |
| B3 | $C_2F_5-O-CF_2-CF_2-CH_2CH_2-OH$ |
| B4 | $C_2F_5-O-(CF_2-CF_2)_2-CH_2CH_2-OH$ |

TABLE 1B-continued

| Compound No. | Structure |
| --- | --- |
| B5 | $C_3F_7-O-CF_2-CF_2-CH_2CH_2-OH$ |
| B6 | $C_3F_7-O-(CF_2-CF_2)_2-CH_2CH_2-OH$ |
| B7 | $C_4F_9-O-CF_2-CF_2-CH_2CH_2-OH$ |
| B6 | $C_4F_9-O-(CF_2-CF_2)_2-CH_2CH_2-OH$ |
| B9 | $C_6F_{13}-O-CF_2-CF_2-CH_2CH_2-OH$ |
| B10 | $C_6F_{13}-O-(CF_2-CF_2)_2-CH_2CH_2-OH$ |

Partially Fluorinated Primary Amines

Amino amides of formula (VIII) and (IX) are also available according to Scheme 5 using partially fluorinated amines $R_f$—$NH_2$.

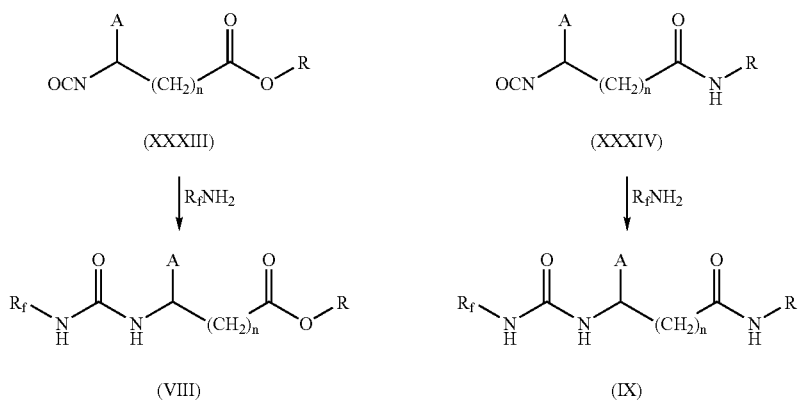

Scheme 5

The partially fluorinated amines are available by synthesis. For instance, 2-perfluoroalkylethylamines can be provided by conversion of 2-perfluoroalkylethyl iodides to azides, followed by reduction of the azides to primary amines with hydrazine/Raney Ni or sodium borohydride/water, as disclosed by Cambon et al, in J. Fluorine Chem., 69 (1994) 115-11. The fluoroalkyl ethylene telomer iodides represented in Scheme 3 and 4 above, can be treated in a similar manner to provide the primary amines corresponding to the alcohols of Table 1A and 1B wherein —OH is replaced with —$NH_2$. The alkyl terminal amino alkynes can provide partially fluorinated triazole amines according to the following scheme.

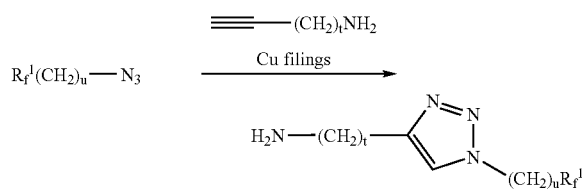

Organogelators and Nanoweb Composites

The compounds of various embodiments of the invention are useful as organogelators, i.e. compounds that can self-assemble into fiber-like morphologies. Upon cooling a hot, homogeneous solution of a thermoreversible gelator in a gelling solvent for example, the gelator molecules associate via intermolecular hydrogen bonds to form fibers, which are bundles of H-bonded gelator molecules. If these fibrous bundles grow to be sufficiently long, they become entangled with one another like covalently-linked polymer chains to gel their solvent medium. The solvent can be removed from the gel to leave behind a network of assembled gelator fibers, a "nanoweb". Hence, organogelators can be used to obtain particular surface effects on porous or solid substrates and can be useful in the formation of nanoweb composites. One aspect of the invention is a composite material comprising a porous support and a porous nanoweb, wherein said porous nanoweb comprises fibrous structures of about 10 nm to about 1000 nm effective average fiber diameter as determined with electron microscopy; said fibrous structures comprising one or more compositions of formula (I).

Porous supports useful in the invention include woven and nonwoven fabrics, sheet materials and films, monolithic aggregates, powders, and porous articles such as frits and cartridges. Porous supports include: woven fabrics comprising glass, polyamides including but not limited to polyamide-6,6 (PA-66), polyamide-6 (PA-6), and polyamide-6,10 (PA-610), polyesters including but not limited to polyethylene terephthalate (PET), polytrimethylene terephthalate, and polybutylene terephthalate (PBT), rayon, cotton, wool, silk and combinations thereof; nonwoven materials having fibers of glass, paper, cellulose acetate and nitrate, polyamides, polyesters, polyolefins including bonded polyethylene (PE) and polypropylene (PP), and combinations thereof. Porous supports include nonwovens fabrics, for instance, polyolefins including PE and PP such as TYVEK® (flash spun PE fiber), SONTARA® (nonwoven polyester), and XAVAN® (nonwoven PP), SUPREL®, a nonwoven spunbond-meltblown-spunbond (SMS) composite sheet comprising multiple layers of sheath-core bicomponent melt spun fibers and side-by-side bicomponent meltblown fibers, such as described in U.S. Pat. Nos. 6,548,431, 6,797,655 and 6,831,025, herein incorporated by reference all trademarked products of E.I. du Pont de Nemours and Company; nonwoven composite sheet comprising sheath-core bicomponent melt spun fibers, such as described in U.S. Pat. No. 5,885,909, herein incorporated by reference; other multi-layer SMS nonwovens that are known in the art, such as PP spunbond-PP meltblown-PP spunbond laminates; nonwoven glass fiber media that are well known in the art and as described in Waggoner, U.S. Pat. No. 3,338,825, Bodendorf, U.S. Pat. No. 3,253,978, and references cited therein, hereby incorporated by reference; and KOLON® (spunbond polyester) a trademarked product of Korea Vilene. The nonwovens materials include those formed by web forming processing including dry laid (carded or air laid), wet laid, spunbonded and melt blown. The nonwoven web can be bonded with a resin, thermally bonded, solvent bonded, needle punched, spun-laced, or stitch-bonded. The bicomponent melt spun fibers, referred to above, can have a sheath of PE and a core of polyester. If a composite sheet comprising multiple layers is used, the bicomponent melt-blown fibers can have a PE component and a polyester component and be arranged side-by-side along the length thereof. Typically, the side-by-side and the sheath/core bicomponent fibers are separate layers in the multiple layer arrangement.

Preferred porous supports include woven fabrics comprising glass, polyamides, polyesters, and combinations thereof; and nonwoven fabrics comprising glass, paper, cellulose acetate and nitrate, polyamides, polyesters, polyolefins, and combinations thereof. Most preferred porous supports include nonwoven bonded PE, PP, and polyester, and combinations thereof.

Other preferred nonwoven porous supports include electrospun nanofiber supports such as described by Schaefer, et al., in US 2004/0038014, hereby incorporated by reference; and electro-blown nanofiber supports disclosed in Kim, WO 2003/080905, hereby incorporated by reference. The nanofiber supports can be self-supporting or can be supported by other porous support layers. Preferably, the electropsun fiber supports are nanofiber supports comprising nanofibers with an effective fiber diameter in the range of about 20 nm to about 1 μm, and preferably about 100 nm to about 750 nm. Nanofiber supports useful in the invention include those derived from electro-spinning of polyester, polyamide, cellulose acetate, polyvinylidene fluoride (PVdF), polyacrylonitrile (PAN), polysulfone, polystyrene (PS), and polyvinyl alcohol (PVA). A preferred nanofiber porous support is incorporated into a layered structure comprising one or more other porous supports or scrims, for instance, nonwoven bonded PE or PP, and one or more layers of nanofiber, such as described in U.S. patent application Ser. No. 10/983,513 filed in November 2004, hereby incorporated by reference.

Solid substrates useful for the invention are stone, masonry, concrete, unglazed tile, brick, porous clay, granite, limestone, grout, mortar, marble, wood, gypsum board, terrazzo, or composite materials.

An organogelator is defined herein to include a non-polymeric organic compound whose molecules can establish, between themselves, at least one physical interaction leading to a self-assembly of the molecules in a carrier fluid, with formation of a 3-D network, or a "nanoweb gel", that is responsible for gelation of the carrier fluid. The nanoweb gel may result from the formation of a network of fibrous structures due to the stacking or aggregation of organogelator molecules. Depending on the nature of the organogelator, the fibrous structures have variable dimensions that may range up to one micron, or even several microns. These fibrous structures include fibers, strands and/or tapes.

The term "gelling" or "gelation" means a thickening of the medium that may result in a gelatinous consistency and even in a solid, rigid consistency that does not flow under its own weight. The ability to form this network of fibrous structures, and thus the gelation, depends on the nature (or chemical structure) of the organogelator, the nature of the substituents, the nature of the carrier fluid, and the particular temperature, pressure, concentration, pH, shear conditions and other parameters that may be used to induce gelation of the medium. The nanoweb gels can be reversible. For instance, gels formed in a cooling cycle may be dissipated in a heating cycle. This cycle of gel formation can be repeated a number of times since the gel is formed by physical, non-covalent interactions between gelator molecules, such as hydrogen bonding.

A composition in one embodiment of the invention can be made using a nanoweb gel that comprises a nanoweb phase and a fluid phase, which, upon removal of the fluid, forms a porous interpenetrating nanoweb. The applicants have found that this capability is strongly dependent upon the particular structural characteristics of the organogelator and particular processing parameters including the nature of the solvent, temperature, gelator concentration, method of solvent removal, and the nature of the porous support.

The physical interactions of the organogelators are diverse and may include interactions chosen from hydrogen-bonding interactions, π-interactions between unsaturated rings, dipolar and van der Waals interactions, and coordination bonding with organometallic derivatives. In general, the non-covalent forces are weak compared to covalent bonds, which makes them reversible, and it requires that several of them be combined to form a strong association. For example, as discussed in Goshe, et al. (Proc. Nat. Acad. Sci. USA (2002) 99, 4823), the energy of a covalent C—C bond is 350 kJ/mol, while the energy of a hydrogen bond ranges from 4 to 120 kJ/mol, and that of a π-stack from 4 to 20 kJ/mol. The establishment of these interactions may often be promoted by the architecture of the molecule, such as by one or more heteroatom-hydrogen bonds, aromatic rings, unsaturation, bidentate metal coordination sites, and favorable packing geometries. In general, each molecule of an organogelator can establish several types of physical interaction with a neighboring molecule. Thus, in one embodiment, the organogelator preferably comprises at least one conjugated group capable of establishing at least two hydrogen bonds; at least one group having at least two aromatic rings in conjugation; at least one group having 14-atom aromatic system; or at least one group capable of bidentate coordination with a metal ion.

Solvents and specific conditions for forming gels of many organogelators are available in the patent and scientific literature. However, one skilled in the art will recognize that many specific gelators may require some preliminary gelling experimentation. For such cases, a methodology has been developed for matching a solvent system with specific gelators to allow efficient gel formation. In general, if the gelator is too soluble, it will dissolve without forming a gel even at high concentrations. If the gelator is not soluble enough, it may or may not dissolve at high temperature, but precipitate again as the temperature is lowered. Ideally, the organogelator should dissolve in a solvent at some temperature and assemble into a network upon cooling. Preferably the gelators have solubility in a solvent system of about 0.1 to 5 wt % at a temperature/pressure above the gel point. Changing the temperature and/or pressure, adjusting the solvent composition, adjusting the pH, altering the shear-state of thixotropic systems, or a combination of parameters can be used to induce gelling.

A simple screening protocol for evaluating thermo-reversible gels allows evaluation of a specific gelator with different solvents in parallel using a reactor block. In a typical set-up, 2 wt % slurries of the organogelator in solvents of varying polarities can be prepared, for example a series may include: water, n-butanol, ethanol, chloroform, toluene, and cyclohexane. The vials are then placed in a reactor block for 1 h while stirring at a temperature close to the boiling point of the solvent to induce dissolution. In the case of some gelators, for instance, urea-based gelators, additives such as lithium salts, for instance lithium nitrate, can be added in small amounts (0.1 to about 10 wt %, based on the amount of organogelator) as described in U.S. Pat. No. 6,420,466, hereby incorporated by reference. Upon cooling, gelation may occur and is evident by formation of a translucent to opaque appearance without the formation of solid crystals, and/or a significant increase in viscosity. If gelation does not occur, one can screen different solvents or solvent mixtures as well as different additives and additive levels. If a gelator sample is soluble in a given solvent, but gelation does not occur, then one can either raise the gelator concentration to, for instance, 3 or 5 wt % and repeat the heating cycle, or one can lower the solubility of the compound by using a solvent mixture of lower polarity.

Preferred solvents for H-bonded organogelators are those having H-bonding capability that allows disruption of intermolecular H-bonding between solute molecules. Water, ammonia, alcohols, sulfoxides, esters, ethers, amines, amides, and lactams are useful. H-bonded organogelators often exhibit very high solubility in the lower alcohols such as methanol and ethanol. Whereas H-bonded organogelators often exhibit lesser solubility in the higher aliphatic and cyclic alcohols including propanol, butanol, hexanol, cyclohexanol and isomers thereof, making them more desirable for use as gelating solvents. Specific solvents that are especially useful in forming gelling mixtures include: water, the lower aliphatic and cyclic alcohols such as ethanol, isopropyl alcohol, butanol, hexanol, cyclohexanol, cyclopentanol, and octanol; aliphatic and aromatic hydrocarbons such as hexane, cyclohexane, heptane, octane, toluene, xylenes, and mesitylene; amides and lactams such as N-methylpyrrolidone, pyrrolidone, caprolactam, N-methyl caprolactam, dimethyl formamide, and dimethyl acetamide; ethers such as dibutyl ether, dipropyl ether, methyl butyl ether; ether alcohols such as 2-methoxyethanol, 2-butoxyethanol, and others in the class of ethers known as CELLUSOLVES®; esters such as ethyl acetate, butyl acetate and the like; aliphatic and aromatic halocarbons such as dichloromethane, 1,2-dichloroethane, 1,1,1-trichloroethane and dichlorobenzene. Butanol, and especially n-butanol, is a preferred solvent for use in the process of the invention.

The gelling mixture, as applied to a solid or porous support, can be in the form of: a homogeneous isotropic solution; a gel that can be shear-thinned (thixotropic) to form a fluidized gel; or a gel in the form of a film, sheet or powder that can be melted to form a fluidized gel. Formulation of a suitable gelling mixture to depends upon the methods anticipated for applying the gelling mixture and gelling the impregnated or coated support. For instance, in a preferred embodiment the gelling mixture is a gel that can be shear-thinned prior to, or during, application to form a fluidized gel. The fluidized gel can then penetrate a porous support to provide an impregnated support.

In another preferred embodiment the gelling mixture is a homogeneous isotropic solution that, if so desired, is heated above ambient conditions. After applying the solution to provide a coated or impregnated support, the treated support can be cooled to induce gelation. Suitable gelling mixtures preferably comprise 0.01 to 20 wt % of one or more organogelators, and preferably, 0.5 to 5 wt %, with the remainder being solvent and other processing aids, for instance lithium salts.

Applying the gelling mixture to a solid or porous support can be done by a variety of methods including one or more of the steps of: spraying, coating, blading, casting laminating, rolling, printing, dipping, and immersing; and allowing gravity, diffusion, and/or flow through of the gelling mixture into the porous support, and, optionally, applying pressure, heat or vacuum. Spraying, coating, blading, casting and immersing are preferred methods for applying thixotropic gels and spraying and blading are most preferred. Laminating and heating is a preferred method for applying solid gels in the form of films. Spraying, coating, blading, casting, printing and immersing or dipping are preferred methods for applying homogeneous isotropic solutions. In some instances, it is advantageous to remove excess gelling mixture from the surface of a porous support, such as by scraping or the like.

Gelling the treated support can be accomplished by a variety of methods depending upon the nature of the gelling mixture. In one preferred embodiment, wherein the gelling mixture is a thermo-reversible gel, the gelling step comprises cooling of a homogeneous solution of the gelling mixture in the impregnated support. The gelling mixture can be preheated to provide a homogeneous solution or can be cooled from ambient temperature, if so desired. Another preferred embodiment, wherein the gelling mixture is a gel applied with shearing, the gelling step can comprise abating the shearing in the impregnated support. This can be accomplished by allowing the impregnated support to sit for a period of time in the absence of shear. In another embodiment, wherein the gelling mixture is sensitive to pH, the impregnated support can be subjected to a change in pH. In other embodiments the solvent can be modified by addition of a non-solvent in a solvent exchange or partially removed to provide a gel.

Drying the gel, or removing the solvent from the gel, will leave behind a porous nanoweb on and/or within a solid or porous support. Drying can be achieved through a variety of routes including freeze drying, ambient drying, oven, radiant and microwave heating, vacuum drying (with or without heat), or critical point drying (CPD). Alternatively the solvent can be exchanged with another fluid, in a fluid-fluid extraction process or a supercritical fluid extraction (SFE), which then can be removed from the gel via one of the aforementioned drying techniques, if so desired.

The drying method can have a profound effect on the resultant nanoweb structure as the various drying methods occur over different time scales, place different stresses on the nanoweb structure, and involve the crossing of different phase boundaries.

In vacuum drying, the driving force for solvent removal from the impregnated material is increased such that the solvent can be removed more readily, and thus without disruption of the assembled nanoweb. Heat can be used in combination with vacuum if it does not disrupt the gelled assembly. Ambient drying is performed at atmospheric pressure and optionally with heat. In freeze drying, the coated or impregnated material is rapidly frozen (on a time scale that does not allow for rearrangement of the gel structure) and solvent is subsequently sublimed away to provide the nanoweb material.

The porous nanoweb coatings can be characterized by a quantitative estimation of the surface tension relative to that of the support. Surface tension is typically characterized by measuring the contact angle of a water droplet or other liquid substance, contacting the surface in the advancing and receding dynamic modes. Contact angles can also be measured in a static mode. This is a well known method for determining surface properties and is discussed in detail in Physical Chemistry of Surfaces, 4th Ed., Arthur W. Adamson, John Wiley & Sons, 1982, pp. 338-361. The water contact angle is a quantitative measurement of the hydrophobicity of a surface. The higher the hydrophobicity, the higher will be the contact angle of the water droplet. Surfaces exhibiting water droplet advancing contact angles of greater than 150° are considered super-hydrophobic. The details of contact angle measurements are discussed in the examples. Preferred nanoweb coatings of the invention are characterized by water droplet advancing contact angle of greater than 130°. Other preferred coatings of the invention are characterized by a static hexadecane droplet contact angle of about 70° or greater, indicating oleophobicity.

The composite materials of various embodiments of the invention can be used as gas-solid filter. The gas can be air, carbon dioxide, oxygen, nitrogen, a noble gas, or any other process gas used in industrial or commercial processes. Air filters are preferred applications of the composite materials. Filters can be in the form of nonwoven pleated or unpleated cartridge filters, glass or other ceramic microfiber filters.

Since the individual organogelator molecules making up the nanoweb are not covalently bonded to one another, there are conditions in which the porous nanoweb can be easily dissolved and removed from the porous support. In applications wherein trapped material is of significant interest, for instance, biological material, radioactive material, etc., the solubility of the nanoweb is a particular advantage, as it can allow release and recovery of the trapped material. Such flexibility can be useful in recycling and recovery of composite materials as well.

The composite materials of various embodiments may also find use in barrier fabric applications, such as for protective clothing or construction wrap, in which good barrier against liquid penetration is provided while maintaining good air and moisture vapor permeability.

These examples are illustrative and are not to be read as limiting the scope of the invention as it is defined by the appended claims.

Materials and Methods

All solvents and reagents, unless otherwise indicated, were purchased from commercial sources and used directly as supplied. 1H,1H,2H,2H-perfluorooctyl amine and 1H,1H,2H,2H-perfluorohexylamine were synthesized from corresponding iodides via the azide followed by reduction using Raney Ni as described in the literature procedure (Trabelsi, H.; Szoenyi, F.; Michelangeli, N.; Cambon, A. *J. Fluorine Chem.*, 1994, 69, 115-117). 2H,2H,3H,3H-perfluorononoyl chloride and 2H,2H,3H,3H-perfluoroheptanoyl chloride were prepared from 1H,1H,2H,2H-perfluorooctyl iodide and 1H,1H,2H,2H-perfluorohexyl iodide by the reaction with Mg followed by treatment with dry-ice and $PCl_5$. 1H,1H,2H,2H-perfluorooctyl isocyanate and 1H,1H,2H,2H-perfluorohexyl isocyanate were prepared the reaction of corresponding acid chloride with trimethylsilylazide ($TMSN_3$) (Jouani, A. M.; Szonyi, F.; Cambon, A., *J. Fluorine Chem.*, 1992, 56, 85-92). $^1H$ and $^{19}F$ NMR spectra were recorded on a Brucker DRX 400 or 500 Spectrometer. Chemical shifts have been reported in ppm relative to an internal reference ($CDCl_3$, $CFCl_3$ or TMS). All melting points reported are uncorrected.

Compound A6

Ethylene (25 g) was introduced to an autoclave charged with $C_4F_9CH_2CF_2I$ (217 g) and d-(+)-limonene (1 g), and the reactor heated at 240° C. for 12 h. The product was isolated by vacuum distillation to provide $C_4F_9CH_2CF_2CH_2CH_2I$.

Fuming sulfuric acid (70 mL) was added slowly to 50 g of $C_4F_9CH_2CF_2CH_2CH_2I$ and mixture stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate and distilled to provide compound A6 (b.p. 54~57° C. at 2 mmHg, 266 Pa).

Compound A7

Ethylene (18 g) was introduced to an autoclave charged with $C_4F_9(CH_2CF_2)_2I$ (181 g) and d-(+)-limonene (1 g), and the reactor heated at 240° C. for 12 h. Product was isolated by vacuum distillation to provide $C_4F_9(CH_2CF_2)_2CH_2CH_2I$.

$C_4F_9(CH_2CF_2)_2CH_2CH_2I$ (10 g) and N-methyl-formamide (8.9 mL) were heated to 150° C. for 26 h. The reaction was cooled to 100° C., followed by the addition of water to separate the crude ester. Ethyl alcohol (3 mL) and p-toluene sulfonic acid (0.09 g) were added to the crude ester, and the reaction was stirred at 70° C. for 15 min. Then ethyl formate and ethyl alcohol were distilled out to give a crude product. The crude alcohol was dissolved in ether, washed with aqueous sodium sulfite, water, and brine in series, and dried over magnesium sulfate. The product was then distilled to give compound A7, bp 90~94° C. at 2 mm Hg, 266 Pa.

Compound A11

Ethylene (15 g) was introduced to an autoclave charged with $C_6F_{13}CH_2CF_2I$ (170 g) and d-(+)-limonene (1 g), and then the reactor was heated at 240° C. for 12 h. Product was isolated by vacuum distillation to provide $C_6F_{13}CH_2CF_2CH_2CH_2I$.

Fuming sulfuric acid (129 mL) was added slowly to $C_6F_{13}CH_2CF_2CH_2CH_2I$ (112 g). The mixture was stirred at 60° C. for 1.5 h. Then the reaction was quenched with ice-cold 1.5 wt % aqueous $Na_2SO_3$ and heated at 95° C. for 0.5 h. The bottom layer was separated and washed with 10% sodium acetate aqueous solution and distilled to provide compound A11, mp 38° C.

Compound A12

Ethylene (56 g) was introduced to an autoclave charged with $C_6F_{13}(CH_2CF_2)_2I$ (714 g) and d-(+)-limonene (3.2 g), and the reactor heated at 240° C. for 12 h. Product was isolated by vacuum distillation to provide $C_6F_{13}(CH_2CF_2)_2CH_2CH_2I$.

$C_6F_{13}(CH_2CF_2)_2CH_2CH_2I$ (111 g) and N-methyl-formamide (81 mL) were heated to 150° C. for 26 h. The reaction was cooled to 100° C., followed by the addition of water to separate the crude ester. Ethyl alcohol (21 mL) and p-toluene sulfonic acid (0.7 g) were added to the crude ester, and the reaction was stirred at 70° C. for 15 min. Then ethyl formate and ethyl alcohol were distilled out to give a crude alcohol. The crude alcohol was dissolved in ether, washed with aqueous sodium sulfite, water, and brine in turn, then dried over magnesium sulfate. The product was distilled under vacuum to provide compound A12, mp 42° C.

Compound B1

$CF_3OCF_2CF_2I$ (285 g, 0.91 mol) and benzoyl peroxide (12 g) were charged under nitrogen to a pressure vessel. A series of three vacuum/nitrogen gas sequences were then executed at −50° C., after which ethylene (69 g, 2.46 mol) was introduced. The vessel was heated for 24 hours at 110° C. The autoclave was cooled to 0° C. and opened after degassing. Then the product was collected in a bottle. Two runs were combined and the product was distilled giving 292 g of $CF_3OCF_2CF_2CH_2CH_2I$ in 50% yield. The boiling point of the product was 56~60° C. at 60 mm Hg pressure (7980 Pa).

A mixture of $CF_3OCF_2CF_2CH_2CH_2I$, (92 g, 0.27 mol) and N-methyl-formamide (119 mL), was heated to 150° C. for 26 hours. Then the reaction was cooled to 100° C., followed by the addition of water to separate the crude ester. Ethyl alcohol (30 mL) and p-toluene sulfonic acid (1.03 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 44 g of $CF_3OCF_2CF_2CH_2CH_2OH$ (compound B1) in 71% yield.

Compound B3

$C_2F_5OCF_2CF_2I$ (116 g, 0.32 mol) and benzoyl peroxide (4 g) were charged under nitrogen. A series of three vacuum/N2 gas sequences was then executed at −50° C. and ethylene (24 g, 0.86 mol) was introduced. The vessel was heated for 24 hour at 110° C. The autoclave was cooled to 0° C. and opened after degassing. Then the product was collected in a bottle. Six runs were combined, and the product was distilled giving 470 g of $C_2F_5OCF_2CF_2CH_2CH_2I$ in 64% yield. The boiling point was 75~77° C. at 25 mm Hg pressure (3325 Pa).

The flask was charged with 130 g of $C_2F_5OCF_2CF_2CH_2CH_2I$, 643 mL of the N-methyl pyrrolidone and 48 mL of deionized (DI) water. The reaction mixture was heated to 132 C for 20 hours. DI water was added and the lower layer was separated. The lower layer was dissolved in ether, washed with saturated sodium sulfite, and dried over anhydrous sodium sulfate. After rotary vaporization, 48 g of $C_2F_5OCF_2CF_2CH_2CH_2OH$ (compound B3) was obtained by distillation in 52% yield. The boiling point was 70~72° C. at 60 mm Hg pressure (7980 Pa).

Compound B5 n-$C_3F_7OCF_2CF_2I$ (100 g, 0.24 mol) and benzoyl peroxide (3 g) were charged under nitrogen to a pressure vessel. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg pressure (3325 Pa).

A mixture of n-$C_3F_7OCF_2CF_2CH_2CH_2I$ (300 g, 0.68 mol) and N-methyl-formamide (300 mL), was heated to 150° C. for 26 h. The mixture was cooled to 100° C., followed by the addition of water to separate the crude ester. Ethanol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of CF₃OCF₂CF₂CH₂CH₂OH (compound B5) in 85% yield. The boiling point was 71~73° C. at 40 mmHg (5320 Pa).

EXAMPLE 1

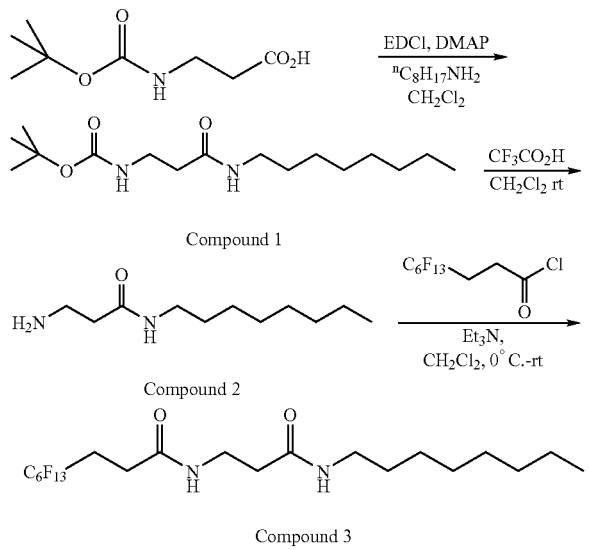

Compound 1

Compound 2

Compound 3

This example illustrates the synthesis of compound 3.

A mixture of dichloromethane (350 mL), N-BOC-β-alanine (8.50 g, 45.0 mmol), 1-[3-(dimethylamino)propyl]-3-ethylcarbodiimide hydrochloride (EDCl) (8.6 g, g, 45.0 mmol) and 4-(dimethylamino)pyridine (5.49 g, 45.0 mmol) was stirred for 10 min at room temperature (RT) followed by addition of octylamine (5.71 g, 45.0 mmol). The mixture was stirred for 12 h at RT. The mixture was washed with 5% HCl (2×100 mL), saturated NaHCO₃ solution (1×100 mL) and brine (1×50 mL). The resulting organic layer was dried (MgSO₄) and concentrated to provide compound 1 as a white crystalline solid (11.6 g, 38.6 mmol, 86%): Mp 67.5-68.4° C.; $^1$H NMR (methanol-d4): δ 3.33 (m, 4H), 3.17 (t, J=7.0 Hz, 2H), 2.36 (t, J=6.5 Hz, 2H), 1.50 (quintet, J=7.0 Hz, 2H), 1.45 (s, 9H), 1.34 (m, 10H), 0.93 (t, J=6.5 Hz, 3H):

A suspension of compound 1 (10.5 g, 35.0 mmol) in dichloromethane (40 mL) was stirred with trifluoroacetic acid (TFA) (31.9 g, 280 mmol) at RT for 3 h. Chloroform (100 mL) was added and the bulk of the solvents and TFA evaporated under vacuum. The resulting trifluoro acetate salt was suspended in dichloromethane (50 mL) and stirred with drop wise addition of saturated NaHCO₃ solution (200 mL) and the solid formed was filtered. The residue was washed several times with cold water and dried under vacuum to provide compound 2 (6.5 g, 32.5 mmol, 93%): Mp 142-143.5° C.

To a mixture of compound 2 (1.0 g, 5.0 mmol), dichloromethane (20 mL) and triethyl amine (0.526 g, 0.52 mmol) under an N₂ purge was added 2H,2H,3H,3H-perfluorononoyl chloride (2.13 g, 5.2 mmol) and the mixture stirred for 5 h at RT. The bulk of the dichloromethane was evaporated and the solid obtained was taken in ethyl acetate (60 mL) and washed with 2% HCl (2×30 mL), water (1×30 mL) and brine (1×30 mL). The resulting organic layer was dried (MgSO₄) and concentrated to provide compound 3 as a white solid (2.46 g, 86%): $^1$H NMR (methanol-d4), δ 3.46 (t, J=7.2 Hz, 2H), 3.17 (t, J=7.0 Hz, 2H), 2.58 (m, 2H), 2.40 (t, J=6.5 Hz, 4H), 1.50 (quintet, J=7.0 Hz, 2H), 1.34 (m, 10H), 0.93 (t, distorted, 3H);

$^{19}$F NMR (methanol d4), δ −82.8 (m, 3F), −115.9 (m, 2F), −123.3 (s, 2F), −124.3 (s, 2F), −125.0 (m, 2F), −127.7 (m, 2F).

EXAMPLE 2

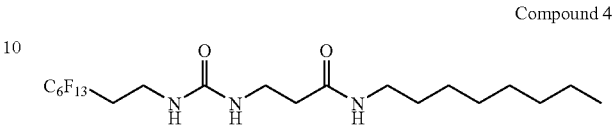

Compound 4

This example illustrates the synthesis of compound 4.

To a mixture of compound 2 (0.822 g, 4.11 mmol), dichloromethane (20 mL) and triethyl amine (0.02 g, 0.2 mmol) under a N₂ purge was added 1H,1H,2H,2H-perfluorooctyl-isocyanate (1.75 g, 4.52 mmol) and the mixture stirred for 5 h at RT. The solid product was filtered and washed with cold hexanes (2×5 mL) to provide compound 4 (1.8 g, 74%): Mp 132-136° C.; $^1$H NMR (methanol-d4): δ 3.46 (t, J=7.2 Hz, 2H), 3.39 (t, J=6.4 Hz, 2H), 2.94 (m, 2H), 2.60 (t, J=6.0 Hz, 2H), 2.39 (m, 2H), 1.53 (m, 2H), 1.34 (bs, 10H), 0.92 (t, distorted, 3H); $^{19}$F NMR (methanol d4): δ −82.8 (m, 3F), −115.6 (m, 2F), −123.2 (s, 2F), −124.2 (s, 2F), −125.0 (m, 2F), −127.7 (m, 2F).

EXAMPLE 3

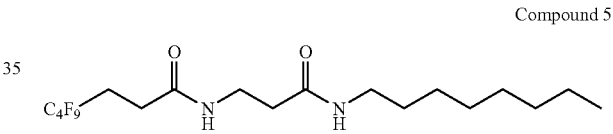

Compound 5

This example illustrates the synthesis of compound 5.

By using a similar procedure as described in example 1, reaction of compound 2 (1.37 g, 6.85 mmol) with 2H,2H,3H,3H-perfluoroheptanoyl chloride (2.13 g, 6.85 mmol) provided compound 5 (2.8 g, 5.90 mmol, 86%): Mp: 99-102° C.; $^1$H NMR (CDCl₃): δ 6.78 (bs, 1H), 5.81 (bs, 1H), 3.56 (q, J=6.4 Hz, 2H), 3.25 (q, J=7.2 Hz, 2H), 2.47 (m, 2H), 2.43 (t, J=5.6 Hz, 4H), 1.51 (quintet, J=7.0 Hz, 2H), 1.30 (m, 10H), 0.901 (t, J=7.5 Hz, 3H); $^{19}$F NMR (CDCl₃): δ −81.6 (m, 3F), −115.3 (m, 2F), −125.0 (m, 2F), −126.6 (m, 2F).

EXAMPLE 4

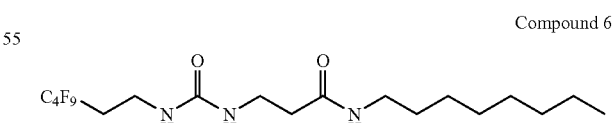

Compound 6

This example illustrates the synthesis of compound 6.

By using a similar procedure as described in example 2, reaction of compound 2 (0.629 g, 3.14 mmol) with 1H,1H,2H,2H-perfluorohexyl isocyanate (1.2 g, 4.15 mmol) provided compound 6 (1.08 g, 67%): $^1$H NMR (methanol-d4): δ 3.46 (t, J=7.2 Hz, 2H), 3.39 (t, J=6.4 Hz, 2H), 3.19 (m, 2H), 2.61 (t, J=6.0 Hz, 2H), 2.39 (m, 2H), 1.53 (m, 2H), 1.34 (bs, 10H), 0.92 (t, distorted, 3H); $^{19}$F NMR (methanol d4): δ −83.0 (m, 3F), −115.8 (m, 2F), −126.1 (m, 2F), −127.6 (m, 2F).

EXAMPLE 5

Compound 7

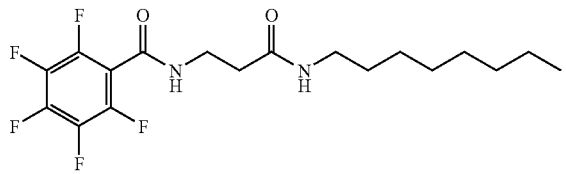

This example illustrates the synthesis of compound 7.

By using a similar procedure as described in example 1, reaction of compound 2 (1.37 g, 6.85 mmol) with pentafluorobenzoyl chloride (1.57 g, 6.85 mmol) provided compound 7 (2.2 g, 5.58 mmol, 82%): Mp: 154-155° C.; $^{1}$H NMR (methanol-d4): δ 3.65 (t, J=6.8 Hz, 2H), 3.19 (t, J=7.2 Hz, 2H), 2.53 (t, J=5.6 Hz, 2H), 1.52 (quintet, J=7.0 Hz, 2H), 1.34 (m, 10H), 0.92 (t, distorted, 3H); $^{19}$F NMR (methanol-d4): δ −144.3 (m, 2F), −155.8 (m, 1F), −164.3 (m, 2F).

EXAMPLE 6

Compound 8

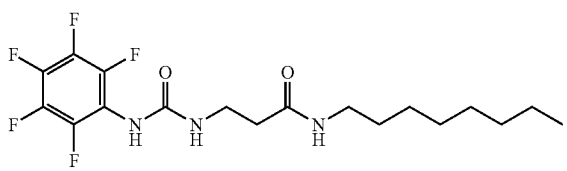

This example illustrates the synthesis of compound 8.

By using a similar procedure as described in example 2, reaction of compound 2 (1.0 g, 5.0 mmol) with pentafluorophenyl isocyanate (1.04 g, 5.0 mmol) provided compound 8 (1.72 g, 84%): Mp 175-176° C.; $^{1}$H NMR (methanol-d4): δ 3.48 (t, J=6.8 Hz, 2H), 3.20 (t, J=7.2 Hz, 2H), 2.45 (t, J=5.6 Hz, 2H), 1.52 (quintet, J=7.0 Hz, 2H), 1.33 (m, 10H), 0.91 (t, J=7.5 Hz, 3H); $^{19}$F NMR (methanol-d4): δ −149.4 (m, 2F), −162.8 (t, J=20.6 Hz, 1F), −167.3 (m, 2F).

EXAMPLE 7

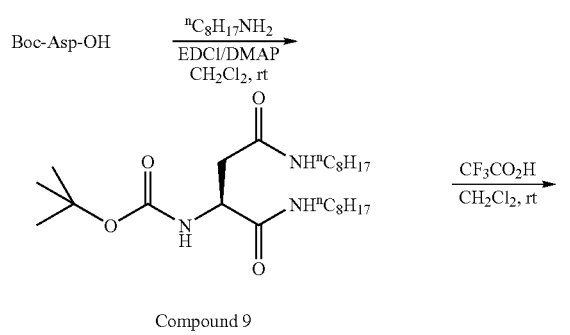

Compound 9

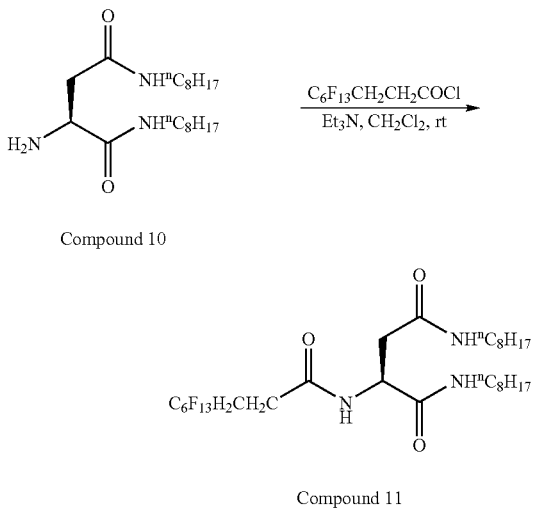

Compound 10

Compound 11

This example illustrates the synthesis of compound 11.

By using a similar procedure as described in example 1, reaction of N-BOC-aspartic acid (10.0 g, 43.1 mmol) with n-octylamine (11.1 g, 86.2 mmol) provided compound 9 (18.8 g, 92%). Mp 112-113° C.

By using a similar procedure as described in example 1, compound 9 (18.6 g, 41.0 mmol) was deprotected using trifluoroacetic acid to obtain compound 10 (13.4 g, 96%). Mp 120.5-122° C.

By using a similar procedure as described in example 1, reaction of compound 10 (1.775 g, 5.0 mmol) with 2H,2H, 3H,3H-perfluoroononoyl chloride (0.438 g, 2.7 mmol) provided compound 11 (2.8 g, 77%): Mp 178-180° C.; $^{1}$H NMR (Acetone-d6) δ 7.52 (bs, 1H), 7.17 (bs, 1H), 7.06 (bs, 1H), 4.55 (m, 1H), 3.02 (bs, 4H), 2.55-2.40 (m, 6H), 1.27 (m, 4H), 1.16 (bs, 20 H), 0.75 (bs, 6H); $^{19}$F NMR (Acetone-d6): δ −82.1 (s, 3F), −115.2 (s, 2F), −122.8 (s, 2F), −123.8 (s, 2F), −124.4 (s, 2F), −127.1 (s, 2F).

EXAMPLE 8

Compound 12

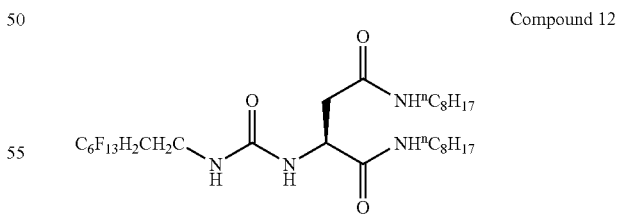

This example illustrates the synthesis of compound 12.

By using a similar procedure as described in example 2, reaction of compound 10 (0.912 g, 2.57 mmol) with 1H,1H, 2H,2H-perfluorooctyl isocyanate (1.16 g, 3.0 mmol) provided compound 12 (1.1 g, 58%): $^{1}$H NMR (methanol-d4): δ 4.54 (t, J=6.8 Hz, 1H), 3.46 (t, J=6.8 Hz, 2H), 3.21 (m, 4H), 2.60 (m, 2H), 2.40 (m, 2H), 1.53 (m, 4H), 1.33 (bs, 20H), 0.922 (t, distorted, 6H); $^{19}$F NMR (methanol-d4): δ −82.8 (m, 3F), −115.6 (s, 2F), −123.2 (s, 2F), −124.2 (s, 2F), −125.0 (s, 2F), −127.6 (m, 2F).

EXAMPLE 9

Compound 13

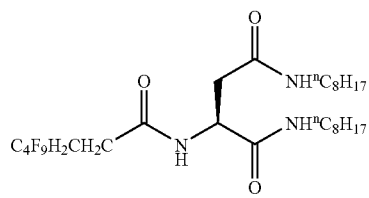

This example illustrates the synthesis of compound 13.

By using a similar procedure as described in example 1, reaction of compound 10 (1.77 g, 5.0 mmol) with 2H,2H,3H,3H-perfluoroheptanoyl chloride (1.55 g, 5.0 mmol) provided compound 13 (1.92 g, 61%): Mp 163.5-165.5° C.; $^1$H NMR (DMF-d7): δ 8.80 (bs, 1H), 8.0 (bs, 1H), 7.96 (bs, 1H), 4.91 (q, J=6.0 Hz, 1H), 3.32 (m, 4H), 2.87-2.70 (m, 4H), 1.63 (m, 4H), 1.45 (bs, 20H), 0.75 (t, distorted, 6H); $^{19}$F NMR (DMF-d7): δ −81.8 (m, 3F), −114.9 (m, 2F), −125.9 (m, 2F), −126.6 (m, 2F).

EXAMPLE 10

Compound 14

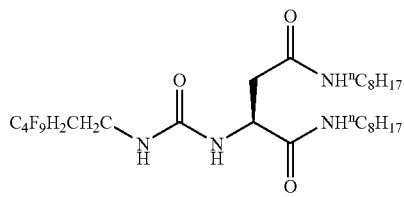

This example illustrates the synthesis of compound 14.

By using a similar procedure as described in example 2, reaction of compound 10 (0.79 g, 2.24 mmol) with 1H,1H,2H,2H-perfluorohexyl isocyanate (1.0 g, 3.26 mmol) provided compound 14 (1.51 g, 71%) $^1$H NMR (methanol-d4): δ 4.54 (t, J=6.8 Hz, 1H), 3.46 (t, J=6.8 Hz, 2H), 3.22 (m, 4H), 2.61 (m, 2H), 2.41 (m, 2H), 1.51 (m, 4H), 1.33 (bs, 20H), 0.922 (t, distorted, 6H); $^{19}$F NMR (methanol-d4): δ −83.0 (m, 3F), −115.8 (m, 2F), −126.0 (m, 2F), −127.6 (m, 2F).

EXAMPLE 11

Compound 15

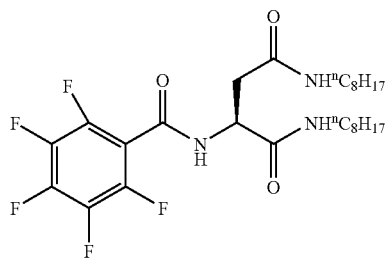

This example illustrates the synthesis of compound 15.

By using a similar procedure as described in example 1, reaction of compound 10 (1.77 g, 5.0 mmol) with pentafluorobenzoyl chloride (1.15 g, 5.0 mmol) provided compound 15 (1.8 g, 66%): Mp 172-183.5° C.; $^1$H NMR (DMF-d7): 69.11 (d, J=8.0 Hz, 1H), 7.88(m 2H), 4.96(q, J=6.8 Hz, 1H), 3.19 (m, 4H), 2.78-2.70 (m, 2H). 1.48 (m, 4H), 1.29 (bs, 20 H), 0.89 (t, distorted, 6H); $^{19}$F NMR (DMF-d7): δ −143.0 (m, 2F), −155.5 (t, J=21.6 Hz, 1F), −163.9 (m, 2F).

EXAMPLE 12

Compound 16

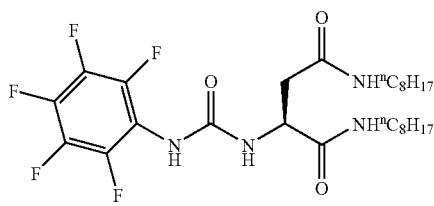

This example illustrates the synthesis of compound 16.

By using a similar procedure as described in example 2, reaction of compound 10 (1.77 g, 5.0 mmol) with pentafluorophenyl isocyanate (1.04 g, 5.0 mmol) provided compound 16 (2.0 g, 71%): $^1$H NMR (DMF-d7): δ 8.74 (m, 1H), 7.57 (bs, 2H), 7.17 (bs, 1H), 4.74 (q, J=6.8 Hz, 1H), 3.35 (m, 4H), 2.86 (dd, J=15.2, 6.0 Hz, 1H), 2.78 (dd, J=15.2, 6.0 Hz, 1H), 1.65 (m, 4H), 1.47 (bs, 20 H), 1.03 (t, distorted, 6H); $^{19}$F NMR (DMF-d7): δ −147.8 (m, 2F), −163.2 (t, J=22.0 Hz, 1F), −168.3 (m, 2F).

EXAMPLE 13

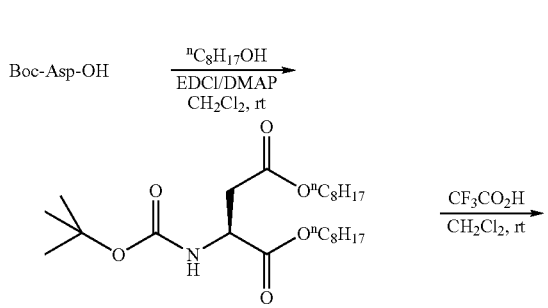

Compound 17

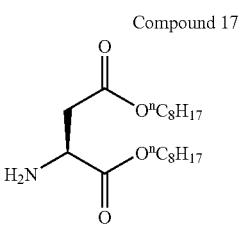

Compound 18

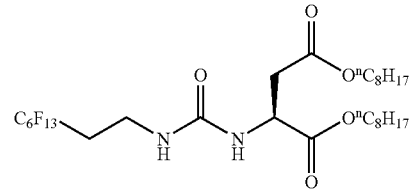

Compound 19

This example illustrates the synthesis of compound 19.

By using a similar procedure as described in example 1, reaction of N-butoxycarbonyl (BOC)-aspartic acid (10.0 g, 43.1 mmol) with n-octanol (11.2 g, 86.2 mmol) provided compound 17 (19.0 g, 96%).

By using a similar procedure as described in example 1, Compound 20 (19.0 g, 41.5 mmol) was deprotected using trifluoroacetic acid to obtain compound 18 (12.1 g, 82%).

To a mixture of compound 21 (1.0 g, 2.8 mmol) in toluene (10 mL) was added bis(trichloroethyl)carbonate (0.277, 0.933 mmol) and heated to 100° C. for 5 h. The reaction mixture was cooled to RT and a solution of 1H,1H,2H,2H-perfluorooctylamine (0.75 g, 2.85 mmol) in toluene (2 mL) was slowly added. The reaction mixture was heated at 70° C. for 8 h followed by aqueous work-up to provide compound 19 (1.3 g, 71%): $^1$H NMR (CDCl$_3$): δ. 5.34 (bs, 1H), 4.74 (m, 1H), 4.65 (bs, 1H), 4.09-3.97 (m, 4H), 3.47 (t, J=6.4 Hz, 2H), 2.93 (dd, J=16.8, 4.8 Hz, 1H), 2.72 (dd, J=16.8, 4.8 Hz, 1H), 2.27 (m, 2H), 1.53 (m, 4H), 1.20 (m, 20 H), 0.81 (t, J=6.8 Hz, 6H); $^{19}$F NMR (CDCl$_3$): δ. −81.2 (m, 3F), −114.3 (m, 2F), −122.2 (s, 2F), −123.2 (s, 2F), −124.0 (s, 2F), −126.5 (m, 2F).

EXAMPLE 14

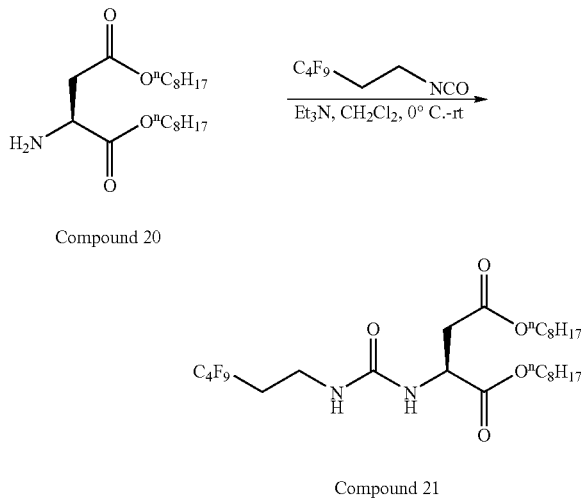

Compound 20

Compound 21

This example illustrates the synthesis of compound 21.

By using a similar procedure as described in example 2, reaction of compound 20 (0.629 g, 3.14 mmol) with 1H,1H,2H,2H-perfluorohexyl isocyanate (1.21 g, 4.21 mmol) provided compound 21 (1.12 g, 67%): $^1$H NMR (CDCl$_3$): δ. 5.70 (bs, 1H), 5.39 (bs, 1H), 4.75 (m, 1H), 4.15-3.4.0 (m, 4H), 3.55 (t, J=6.4 Hz, 2H), 2.97 (dd, J=16.8, 4.8 Hz, 1H), 2.78 (dd, J=16.8, 4.8 Hz, 1H), 2.34 (m, 2H), 1.60 (m, 4H), 1.26 (m, 16H), 0.93 (t, J=6.8 Hz, 6H); $^{19}$F NMR (CDCl$_3$): δ. −81.5 (m, 3F), −114.5 (m, 2F), −122.4 (s, 2F), −123.5 (s, 2F), −124.4 (s, 2F), −126.7 (m, 2F).

EXAMPLE 15

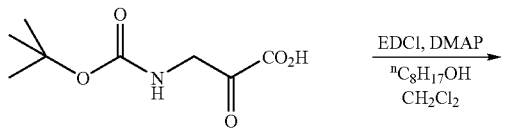

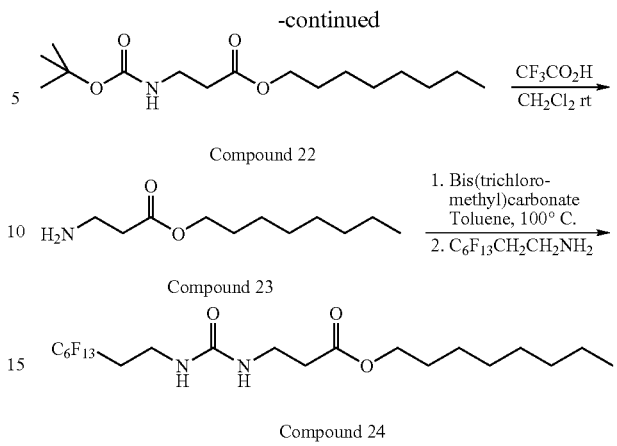

Compound 22

Compound 23

Compound 24

This example illustrates the synthesis of compound 24.

By using a similar procedure as described in example 13, reaction of N-butoxycarbonyl (BOC)-β-alanine (8.5 g, 45.0 mmol) was esterified with n-octanol (5.85 g, 45.0 mmol) provided compound 22 (12.75 g, 94%).

By using a similar procedure as described in example 13, Compound 22 (19.0 g, 41.5 mmol) was deprotected using trifluoroacetic acid to obtain compound 23 (6.8 g, 85%).

By using a similar procedure as described in example 13, successive reactions of compound 23 with bis(trichloroethyl) carbonate (0.554 g, 1.86 mmol) followed by 1H,1H,2H,2H-perfluorooctylamine (0.75 g, 2.85 mmol) produced compound 24 as a pale yellow oil (1.95 g, 62%):

$^1$H NMR (CDCl$_3$): δ 4.06 (t, J=7.2 Hz, 2H), 3.53 (t, J=6.4 Hz, 2H), 3.26 (m, 2H), 2.30 (m, 2H), 1.55 (m, 2H), 1.20 (bs, 10H), 0.81 (t, distorted, 3H);

$^{19}$F NMR (CDCl$_3$): δ −81.2 (m, 3F), −114.4 (m, 2F), −122.2 (s, 2F), −123.2 (m, 2F), −124.0 (m, 2F), −126.5 (m, 2F).

EXAMPLE 16

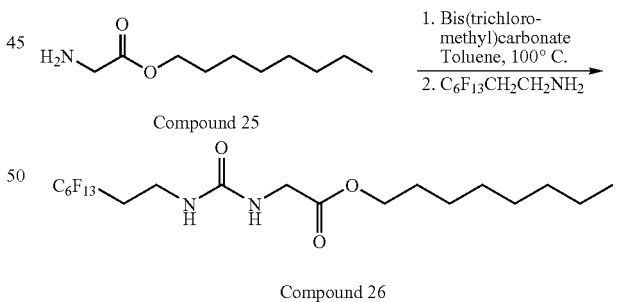

Compound 25

Compound 26

This example illustrates the synthesis of compound 26.

n-Octylglycine hydrochloride (5 g) in water (25 mL) was neutralized with saturated NaHCO$_3$ and extracted with dichloromethane to obtain compound 25. By using a similar procedure as described in example 13, successive reactions of compound 25 with bis(trichloroethyl)carbonate (1.10 g, 3.72 mmol) followed by 1H,1H,2H,2H-perfluorooctylamine (2.49 g, 9.5 mmol) produced compound 26 as a pale yellow oil (2.2 g, 57%). $^{19}$F NMR (CDCl$_3$): δ −81.3 (m, 3F), −114.4 (m, 2F), −122.3 (s, 2F), −123.3 (m, 2F), −124.1 (m, 2F), −126.5 (m, 2F).

EXAMPLE 17

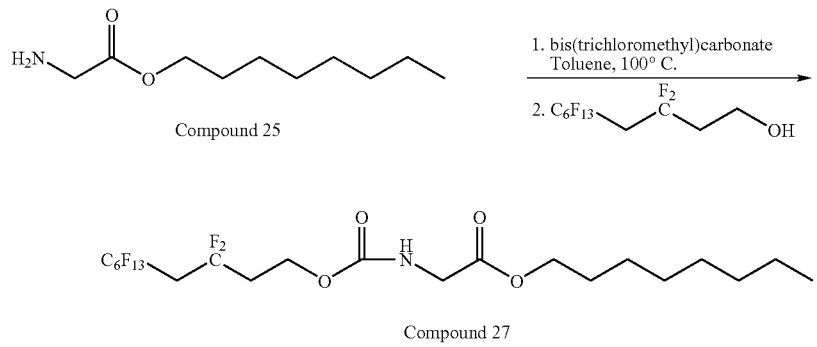

Compound 27

By using a similar procedure as described in example 13, successive reactions of compound 25 with bis(trichloroethyl) carbonate (0.55 g, 1.86 mmol) followed by 1H,1H,2H,2H, 4H,4H-perfluorodecanol (compound A11, 1.71 g, 4.0 mmol) and purification using column chromatography produced compound 27 as a pale yellow oil (1.45 g): $^1$H NMR (CDCl$_3$): δ 5.16 (bs, 1H), 4.17 (t, J=6.2 Hz, 2H), 3.98 (d, J=5.6 Hz, 2H), 3.93 (t, J=7.2 Hz, 2H), 2.86 (m, 2H), 2.32 (m, 2H), 1.64 (m, 2H), 1.31 (m, 10H), 0.91 (t, J=6.8 Hz, 3H); $^{19}$F NMR (CDCl$_3$): δ −81.3 (m, 3F), −92.1 (m, 2F), −112.8 (m, 2F), −122.1 (m, 2F), −123.2 (m, 2F), −123.9 (m, 2F), −126.5 (m, 2F).

EXAMPLE 18

Gelation Test

Generally 0.5-5 wt % of the gelator in an organic solvent (varying polarity from low polar to high polar) in a closed vial was heated (5-10° C. below the boiling point of the solvent) in a reactor block until a clear solution was obtained. The vials were allowed to cool at rt. (either by slow cool by switching of the heat of the reactor block or by transferring the vials in to a constant temperature water bath kept at rt. The state of the solution was evaluated after 2-12 h. Stable gel formation was tested by inversing the vial. The results are summarized in Table 2.

TABLE 2

| | Gelation Conditions | | |
|---|---|---|---|
| Gelator | Wt % gelator | Solvent | Appearance[†] |
| Compound 3 | 3 | Acetone | Partial Gel |
| Compound 4 | 2 | Acetone | Thick Gel |
| Compound 5 | 3 | Acetone or CH$_2$Cl$_2$ | Partial Gel |
| Compound 6 | 3 | Acetone | Thick Gel |
| Compound 7 | 1, 2, 3 | Acetone or THF or CH$_2$Cl$_2$ | Clear Solution |
| | 1, 2, | Hexane | Precipitate |
| Compound 8 | 2 | Acetone, CH$_2$Cl$_2$ | Partial Gel |
| Compound 11 | 3 | Acetone | Thick Gel |
| Compound 12 | 2 | Acetone | Thick Gel |
| | 3 | CH$_2$Cl$_2$ | Hazy Gel |
| Compound 13 | 2 | CH$_2$Cl$_2$ | Hazy Gel |
| | 3 | Acetone | Partial Gel |
| Compound 14 | 3 | Acetone | Partial Gel |

TABLE 2-continued

| | Gelation Conditions | | |
|---|---|---|---|
| Gelator | Wt % gelator | Solvent | Appearance[†] |
| Compound 15 | 2 | Acetone, Methanol | Thick Gel |
| Compound 16 | 0.5, 1, 2, 3 | Acetone | Thick Gel |
| | 0.5 | CH$_2$Cl$_2$ | Transparent |
| | 2 | THF | Gel |
| Compound 19 | 1, 2, 3 | Acetone or CH$_2$Cl$_2$ | Thick Gel |
| Compound 21 | 1, 2, 3 | Acetone or CH$_2$Cl$_2$ | Clear Solution |
| Compound 24 | 2, 3 | Acetone or CH$_2$Cl$_2$ | Clear Solution |
| Compound 26 | 2, 3 | Acetone or CH$_2$Cl$_2$ | Clear Solution |
| | | | Clear Solution |

[†]Hazy gel: solid gel partially transparent. Thick gel. Solid gel not-transparent. Partial gel. solid or semi-moving gel which has some free flowing liquid in it. Precipitate. More like a precipitate than a gel.

EXAMPLE 19

Contact Angle Measurements

Contact angle (CA) measurements to determine the contact angle of both water and hexadecane on a surface were performed using a goniometer. Ramé-Hart Standard Automated Goniometer Model 200 employing DROP image standard software and equipped with an automated dispensing system with 250 μl syringe was used, having an illuminated specimen stage assembly. The goniometer camera was connected through an interface to a computer and this allowed the droplet to be visualized on a computer screen. The horizontal axis line and the cross line could both be independently adjusted on the computer screen using the software.

Prior to contact angle measurement, the sample was placed on the sample stage and the vertical vernier adjusted to align the horizontal line (axis) of the eye piece coincident to the horizontal plane of the sample, and the horizontal position of the stage relative to the eye piece positioned so as to view one side of the test fluid droplet interface region at the sample interface.

To determine the contact angle of the test fluid on the sample, approximately one drop of test fluid was dispensed onto the sample using a 30 μL pipette tip and an automated dispensing system to displace a calibrated amount of the test fluid. For water measurements deionized water was employed, and for oil measurements, hexadecane was suitably employed. Horizontal and cross lines were adjusted via the software in case of the Model 200 after leveling the sample via stage adjustment, and the computer calculated the contact angle based upon modeling the drop appearance. The initial contact angle is that angle determined immediately after dispensing the test fluid to the sample surface. Initial contact angles above 30 degrees are indicators of effective water and oil repellency. Contact angle can be measured after the droplet has been added to a surface (advancing contact angle, abbreviated "Adv CA") or after the droplet has been partially withdrawn from a surface (receding contact angle, abbreviated "Rec CA").

A 1 wt % solution of above compounds in THF were dip coated onto Mylar® PET film (Du Pont Teijin Films, Hopewell, Va. 23860) The films were then air or vacuum dried for 24 h before measuring the contact angles and the values are summarized in Table 3.

TABLE 3

| | Contact angle[a, b] | | | |
| --- | --- | --- | --- | --- |
| | Water | | Hexadecane | |
| Compound | Adv CA | Rec CA | Adv CA | Rec CA |
| Compound 3 | 107 ± 1 | 69 ± 2 | 73 ± 1 | 40 ± 1 |
| Compound 4 | 119 ± 2 | 75 ± 2 | 70 ± 1 | 41 ± 1 |
| Compound 5 | 94 ± 6 | 66 ± 5 | 45 ± 1 | 22 ± 1 |
| Compound 6 | 98 ± 3 | 61 ± 3 | 70 ± 2 | 33 ± 2 |
| Compound 7 | 108 ± 1 | 81 ± 2 | 36 ± 2 | 19 ± 3 |
| Compound 8 | 130 ± 2 | 110 ± 3 | 27 ± 2 | 11 ± 1 |
| Compound 11 | 119 ± 4 | 60 ± 5 | 65 ± 2 | 29 ± 2 |
| Compound 12 | 115 ± 1 | 87 ± 2 | 75 ± 1 | 39 ± 2 |
| Compound 13 | 94 ± 1 | 61 ± 2 | 54 ± 1 | 26 ± 2 |
| Compound 14 | 103 ± 2 | 69 ± 3 | 59 ± 3 | 32 ± 1 |
| Compound 15 | 130 ± 2 | 98 ± 2 | 46 ± 2 | 20 ± 3 |
| Compound 16 | 130 ± 2 | 98 ± 2 | 26 ± 3 | — |
| Compound 19 | 100 ± 1 | 67 ± 1 | 51 ± 3 | 23 ± 3 |
| Compound 21 | 96 ± 2 | 54 ± 3 | 48 ± 2 | 18 ± 3 |
| Compound 24 | 91 ± 2 | 52 ± 4 | 61 ± 2 | 30 ± 1 |
| Compound 26 | 93 ± 3 | 63 ± 2 | 63 ± 3 | 36 ± 1 |
| Compound 27 | 86 ± 3 | 57 ± 3 | 29 ± 2 | 14 ± 1 |

[a]Average of 3 runs at different positions on each sample.
[b]Slight variations observed. Depending on the quality of the film prepared as well as .solvent used. A good gelling solvent for a particular compound and a uniform film results high and consistent values.

EXAMPLES 20-21

Gel-Impregnation Method

Non woven fabrics (about 3.0-3.5 cm squared) were immersed in a suspension of gelator in organic solvent kept in closed reaction flask equipped with a stir bar and temperature controller. The mixtures were heated 5° C. below the boiling point of the solvent for 1-2 hours until clear solutions formed. The flasks were then either rapidly cooled to RT by removing the oil bath or slowly cooled to RT by switching off the heat. Gel formation was usually observed in 2-6 h time and the gels were allowed to age for additional 6 h. The gelator impregnated samples were removed and dried in a vacuum oven at RT or with critical point drying using carbon dioxide. The dried samples were weighed and used for contact angle measurements.

EXAMPLE 20

This example illustrates the gel impregnation of Compound 4 on Tyvek® polyethylene nonwoven fabric (E.I. du Pont de Nemours, Wilmington Del.), By following the procedure as described above, weighed samples of Tyvek® (3.0 cm×3.0 cm) were gel impregnated from a gel obtained by cooling a 2 wt % compound 2 in acetone and dried under vacuum at RT. The dried gel-impregnated Tyvek® nonwoven fabric samples were then used for contact angle measurements. The CA results are summarized in Table 4.

EXAMPLE 21

Figure 2:
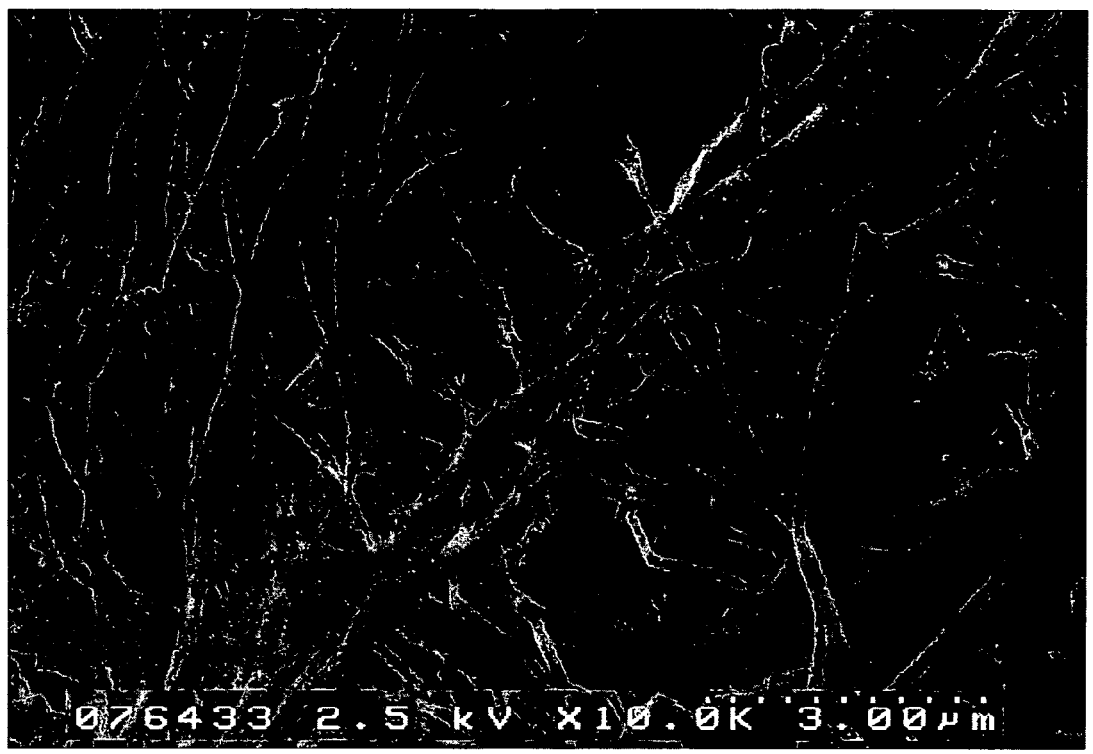
FIG. 2 illustrates a scanning electron micrograph at 10000× magnification of a nanoweb composite of the invention.

Following the procedure as described above, weighed samples of Kolon® spunbound polyester fabric (Korea Vilene Inc., (70 gsm, 3.0 cm×3.0 cm) were gel impregnated from a gel obtained by cooling a 2 wt % compound 4 in acetone and dried under vacuum at RT. FIG. 2 shows a scanning electron micrograph of the nanoweb composite provided, at 1000× magnification. The dried gel-impregnated samples were then used for contact angle measurements. The CA results are summarized in Table 4.

TABLE 4

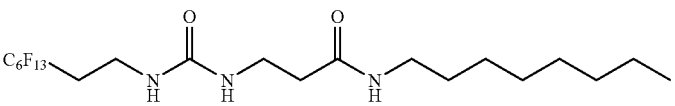

| | Contact angle[a] | | | |
| --- | --- | --- | --- | --- |
| | Water | | Hexadecane | |
| | Adv CA | Rec CA | Adv CA | Rec CA |
| Tyvek ® fabric | 139 ± 5 | 126 ± 1 | 84 ± 4 | 43 ± 1 |
| Kolon ® fabric 70 gsm | 154 ± 3 | 138 ± 2 | 87 ± 4 | 42 ± 2 |

[a]average of 3 runs at different positions on each sample

EXAMPLE 22 COMPARATIVE

For comparison the contact angle values for untreated controls, Tyvek® fabric, Kolon® fabric, 70 gsm, and Whatman® 40 filter paper, contact angles were measured and are summarized in Table 5.

TABLE 5

| | Contact angle[a] | | |
|---|---|---|---|
| | Water[a] | | |
| Untreated samples | Adv CA | Rec CA | Hexadecane |
| Tyvek ® fabric | 108 ± 1 | 78 ± 1 | Completely absorbed |
| Kolon ®-fabric, 70 gsm | 115 ± 4 | 85 ± 4 | Completely absorbed |

[a]average of 3 runs at different positions on each sample

EXAMPLE 23

This example illustrates gel impregnation of compound 11 on Tyvek® nonwoven fabric and Kolon® nonwoven fabric (gsm-70).

Following the procedure described in examples 20 and 21, weighed samples of Tyvek® nonwoven fabric (3.0 cm×3.0 cm) and Kolon® nonwoven fabric, (gsm 70, 3.0 cm×3.0 cm) were gel impregnated from a gel obtained by cooling a 2 wt % solution of compound 11 in acetone. The samples were dried under vacuum at RT. and used for CA measurements summarized in Table 6.

TABLE 6

Compound 11

$C_6F_{13}H_2CH_2C(O)NH-CH(C(O)NH^nC_8H_{17})CH_2C(O)NH^nC_8H_{17}$

| | Contact angle[a] | | | |
|---|---|---|---|---|
| | Water | | Hexadecane | |
| | Adv CA | Rec CA | Adv CA | Rec CA |
| Tyvek ® fabric | 157 ± 1 | 153 ± 2 | 62 ± 2 | 35 ± 4 |
| Kolon ® fabric 70 gsm | 146 ± 3 | 128 ± 1 | 73 ± 4 | 51 ± 5 |

[a]average of 3 runs at different positions on each sample

EXAMPLE 24

This example illustrates gel impregnation of compound 13 on Tyvek® nonwoven fabric and Kolon® nonwoven fabric (gsm-70).

Following the procedure described in examples 20 and 21, weighed samples of Tyvek® nonwoven fabric (3.0 cm×3.0 cm) and Kolon® nonwoven fabric, (gsm 70, 3.0 cm×3.0 cm) were gel impregnated from a gel obtained by cooling a 2 wt % solution of compound 13 in $CH_2Cl_2$. The samples were dried under vacuum at RT. and used for CA measurements summarized in Table 7.

TABLE 7

Compound 13

$C_4F_9H_2CH_2C(O)NH-CH(C(O)NH^nC_8H_{17})CH_2C(O)NH^nC_8H_{17}$

| | Contact angle[a] | | | |
|---|---|---|---|---|
| | Water | | Hexadecane | |
| | Adv CA | Rec CA | Adv CA | Rec CA |
| Tyvek ® fabric | 128 ± 4 | 112 ± 3 | 60 ± 2 | 30 ± 3 |
| Kolon ® fabric 70 gsm | 134 ± 1 | 118 ± 2 | 59 ± 4 | 29 ± 5 |

[a]average of 3 runs at different positions on each sample

EXAMPLE 25

This example illustrates gel impregnation of compound 16 on Tyvek® nonwoven fabric and Kolon® nonwoven fabric (gsm-70).

Following the procedure described in example 19-20, weighed samples of Tyvek® nonwoven fabric (3.0 cm×3.0 cm) and Kolon® nonwoven fabric, (gsm 70, 3.0 cm×3.0 cm) were gel impregnated from a gel obtained by cooling a 1 wt % solution of compound 9 in acetone. The samples were dried under vacuum at RT. and used for CA measurements summarized in Table 8.

TABLE 8

Compound 16

(pentafluorophenyl)-NH-C(O)-NH-CH(C(O)NH$^n$C$_8$H$_{17}$)CH$_2$C(O)NH$^n$C$_8$H$_{17}$

| | Contact angle[a] | | | |
|---|---|---|---|---|
| | Water | | Hexadecane | |
| | Adv CA | Rec CA | Adv CA | Rec CA |
| Tyvek ® fabric | 161 ± 1 | 148 ± 1 | Slowly absorbed in 25 sec | |

TABLE 8-continued

|  | Contact angle[a] | | | |
|---|---|---|---|---|
|  | Water | | Hexadecane | |
| Compound 16 | | | | |
|  | Adv CA | Rec CA | Adv CA | Rec CA |
| Kolon ® fabric 70 gsm | 158 ± 2 | 145 ± 1 | Slowly absorbed in 30 sec | |

[a] average of 3 runs at different positions on each sample

What we claim is:

1. A composition of formula (I)

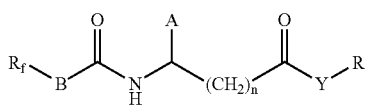

wherein A is selected from the group consisting of: hydrogen, $C_1$-$C_5$ straight and branched chain alkyl, phenyl, benzyl, and —C(O)—Y—R;

Y is independently —O— or —NH—;

n is an integer of 0 to 10;

R is a monovalent group having 1 to 40 carbon atoms;

B is selected from the group consisting of: —O—, —NH—, and a covalent bond;

$R_f$ is a monovalent group is selected from the group consisting of formulas (IIa), (IIb), (IIc) and (IId):

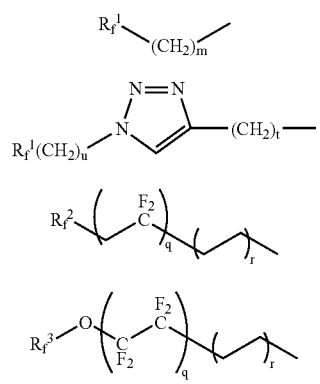

wherein m is an integer of 0 to 4;

u and t are, independently, integers of 1 to 10;

q and r are, independently, integers of 1 to 3;

$R_f^1$ is a $C_1$-$C_6$ linear or branched perfluoroalkyl group, optionally interrupted by one to five ether oxygen atoms, or a $C_6$ perfluorinated aryl group;

$R_f^2$ is a $C_1$-$C_6$ linear or branched perfluoroalkyl group; and $R_f^3$ is a $C_1$ to $C_7$ linear or branched perfluoroalkyl group, optionally interrupted by one to three ether oxygen atoms.

2. The composition of claim 1 wherein $R_f$ is formula (IIa), B is —NH—, m=0 or 2, and $R_f^1$ is a $C_1$-$C_6$ linear or branched perfluoroalkyl group.

3. The composition of claim 1 wherein $R_f$ is formula (IIa), B is a covalent bond, m=0 or 2, and $R_f^1$ is a $C_3$-$C_6$ linear or branched perfluoroalkyl group, optionally interrupted by one to five ether oxygen atoms.

4. The composition of claim 1 wherein $R_f$ is formula (IIa), B=—O—, m=2 to 4, and $R_f^1$ is a $C_2$-$C_6$ linear or branched perfluoroalkyl group.

5. The composition of claim 1 wherein $R_f$ is formula (IIb), B=—O—, and $R_f^1$ is a $C_2$-$C_6$ linear or branched perfluoroalkyl group.

6. The composition of claim 1 wherein $R_f$ is formula (IIc), B=—O—, and $R_f^2$ is a $C_2$-$C_6$ linear perfluoroalkyl group.

7. The composition of claim 1 wherein $R_f$ is formula (IId) and $R_f^3$ is a $C_3$-$C_6$ linear or branched perfluoroalkyl group.

8. The composition of claim 1 wherein A is hydrogen or —C(O)—Y—R; Y is —NH— and R is a $C_6$ to $C_{18}$ linear or branched alkyl group.

9. The composition of claim 1 wherein R is selected from the group consisting of: $C_1$-$C_{18}$ linear or branched alkyl groups; $C_1$-$C_{18}$ linear or branched alkyl groups having, or interrupted by, a $C_4$-$C_{16}$ cycloaliphatic group; $C_1$-$C_{18}$ linear or branched alkyl groups having, or interrupted by, a $C_4$-$C_{16}$ aromatic group; $C_1$-$C_{18}$ linear or branched alkyl groups having, or interrupted by, a $C_4$-$C_{16}$ cycloaliphatic group and a $C_4$-$C_{16}$ aromatic group; $C_4$-$C_{16}$ cycloaliphatic group; a $C_4$-$C_{16}$ aromatic group; and $C_4$-$C_{16}$ cycloaliphatic group having a $C_4$-$C_{16}$ aromatic group; wherein each aromatic group is optionally substituted with one or more Cl or Br; each alkyl and cycloaliphatic group is optionally substituted with one or two carbon-carbon double bonds; each group is optionally interrupted by one to four heteroatoms selected from the group: —O— and —$NR^3$—; and each group is optionally interrupted by one to four linkers selected from the group —S—, —N═, —OC(O)—, —C(O)$NR^3$—, —OC(O)$NR^3$—, —$NR^3$C(O)$NR^3$—; wherein $R^3$ is selected from the group consisting of: hydrogen and $C_1$-$C_4$ alkyl group.

10. A composite material comprising a porous support and a porous nanoweb, wherein said porous nanoweb comprises fibrous structures of about 10 nm to about 1000 nm effective average fiber diameter as determined with electron microscopy; said fibrous structures comprising one or more compositions of claim 1.

11. The composite material of claim 10 wherein the porous support is selected from the group consisting of woven fabrics comprising glass, polyamides, polyesters, and combinations thereof; and nonwoven fabrics comprising glass, paper, cellulose acetate and nitrate, polyamides, polyesters, polyolefins, and combinations thereof.

12. The composite material of claim 10 wherein the composition forms a coating on the porous support.

13. A solid substrate to which has been applied a composition of claim 1.

14. The solid substrate of claim 13 that is selected from the group consisting of stone, masonry, concrete, unglazed tile, brick, porous clay, granite, limestone, grout, mortar, marble, wood, gypsum board, terrazzo, or composite materials.

* * * * *